US010447949B2

(12) United States Patent
Kobayashi

(10) Patent No.: US 10,447,949 B2
(45) Date of Patent: Oct. 15, 2019

(54) ENDOSCOPE APPARATUS, METHOD OF OPERATING ENDOSCOPE APPARATUS, AND RECORDING MEDIUM

(71) Applicant: OLYMPUS CORPORATION, Tokyo (JP)

(72) Inventor: Eiichi Kobayashi, Tokyo (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 15/948,264

(22) Filed: Apr. 9, 2018

(65) Prior Publication Data
US 2018/0234646 A1 Aug. 16, 2018

Related U.S. Application Data

(63) Continuation of application No. PCT/JP2016/079463, filed on Oct. 4, 2016.

(30) Foreign Application Priority Data

Oct. 16, 2015 (JP) ................................ 2015-204496

(51) Int. Cl.
| | |
|---|---|
| *H04N 5/353* | (2011.01) |
| *A61B 1/045* | (2006.01) |
| *H04N 5/225* | (2006.01) |
| *H04N 5/235* | (2006.01) |
| *H04N 5/345* | (2011.01) |
| *H04N 5/369* | (2011.01) |

(Continued)

(52) U.S. Cl.
CPC ........... *H04N 5/3532* (2013.01); *A61B 1/045* (2013.01); *A61B 1/0684* (2013.01);
(Continued)

(58) Field of Classification Search
CPC ........................... H04N 5/3532; H04N 5/2352
See application file for complete search history.

(56) References Cited

U.S. PATENT DOCUMENTS

| | | | |
|---|---|---|---|
| 6,864,916 B1* | 3/2005 | Nayar | ........ H04N 5/2355 348/224.1 |
| 8,189,069 B2* | 5/2012 | Ogawa | ........ H04N 5/23232 348/229.1 |

(Continued)

FOREIGN PATENT DOCUMENTS

| | | |
|---|---|---|
| EP | 2698985 A1 | 2/2014 |
| JP | 2002-049083 A | 2/2002 |

(Continued)

OTHER PUBLICATIONS

International Search Report dated Dec. 27, 2016 issued in PCT/JP2016/079463.

*Primary Examiner* — James M Pontius
(74) *Attorney, Agent, or Firm* — Scully Scott Murphy & Presser, P.C.

(57) ABSTRACT

An endoscope apparatus includes an imaging element, a video signal generating circuit, an illuminator, a light quantity detector, and one or more controllers. An imaging area in which a plurality of pixels are disposed includes a scanning area. The one or more controllers control the imaging element such that at least parts of exposure periods of the pixels disposed in at least a part of the scanning area overlap each other, in a case in which the light quantity is less than a predetermined quantity. The one or more controllers control the illuminator such that the light source is turned on in a period in which at least parts of the exposure periods of the pixels disposed in at least a part of the scanning area overlap each other, in a case in which the light quantity is less than the predetermined quantity.

14 Claims, 13 Drawing Sheets

(51) Int. Cl.
*G02B 23/24* (2006.01)
*A61B 1/06* (2006.01)
*H04N 5/3745* (2011.01)
*H04N 7/18* (2006.01)
*H04N 13/207* (2018.01)

(52) U.S. Cl.
CPC ....... *G02B 23/2484* (2013.01); *H04N 5/2256* (2013.01); *H04N 5/2351* (2013.01); *H04N 5/2352* (2013.01); *H04N 5/2353* (2013.01); *H04N 5/2354* (2013.01); *H04N 5/3452* (2013.01); *H04N 5/3696* (2013.01); *H04N 5/37452* (2013.01); *G02B 23/2469* (2013.01); *H04N 7/183* (2013.01); *H04N 13/207* (2018.05); *H04N 2005/2255* (2013.01)

(56) References Cited

U.S. PATENT DOCUMENTS

| | | | | |
|---|---|---|---|---|
| 2004/0183921 | A1* | 9/2004 | Ueda | G01N 21/6458 348/222.1 |
| 2004/0214099 | A1* | 10/2004 | Matsumoto | H04N 1/1903 430/24 |
| 2008/0219585 | A1* | 9/2008 | Kasai | H04N 5/2351 382/274 |
| 2009/0086073 | A1* | 4/2009 | Kobayashi | H04N 5/3597 348/302 |
| 2010/0128159 | A1* | 5/2010 | Yamashita | H04N 5/35563 348/311 |
| 2011/0285897 | A1* | 11/2011 | Fujii | G03B 7/093 348/345 |
| 2013/0050456 | A1 | 2/2013 | Sakurai et al. | |
| 2018/0097984 | A1* | 4/2018 | Kobayashi | H04N 5/35581 |

FOREIGN PATENT DOCUMENTS

| | | |
|---|---|---|
| JP | 2006-325741 A | 12/2006 |
| JP | 2013-046672 A | 3/2013 |
| JP | 2013-118698 A | 6/2013 |
| JP | 2014-153655 A | 8/2014 |
| JP | 2014-204198 A | 10/2014 |
| WO | WO 2013/157368 A1 | 10/2013 |

* cited by examiner

ENDOSCOPE APPARATUS, METHOD OF OPERATING ENDOSCOPE APPARATUS, AND RECORDING MEDIUM

Priority is claimed on Japanese Patent Application No. 2015-204496, filed on Oct. 16, 2015, and the present application is a continuation application based on PCT/JP 2016/079463 filed on Oct. 4, 2016, and the contents of the Japanese Patent Application and the PCT application described above are incorporated herein by reference.

BACKGROUND

Technical Field

The present invention relates to an endoscope apparatus, a method of operating an endoscope apparatus, and a recording medium.

Background Art

Endoscope apparatuses performing three-dimensional measurement for a subject on the basis of images of the subject acquired by an endoscope are used. For example, an endoscope apparatus performing stereo measurement on the basis of two images having a parallax is disclosed in Japanese Unexamined Patent Application, First Publication No. 2006-325741. In the endoscope apparatus disclosed in Japanese Unexamined Patent Application, First Publication No. 2006-325741, a distance to a subject at a designated position on one of two images acquired in real time is displayed in real time.

As a general method of driving an imaging element used for an endoscope apparatus, there is a rolling shutter. The imaging element includes a plurality of pixels disposed in a matrix pattern. In the rolling shutter, the generation of an imaging signal and the reading thereof are performed for each row in the arrangement of the plurality of pixels.

SUMMARY

According to a first aspect of the present invention, an endoscope apparatus includes an imaging element, a video signal generating circuit, an illuminator, a light quantity detector, and one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels in each row in the scanning area. The video signal generating circuit generates video signals from the imaging signals. The illuminator includes a light source generating illumination light emitted to the subject. The light quantity detector detects a light quantity at a place in which the imaging element is disposed. The one or more controllers control the imaging element such that at least parts of exposure periods of the pixels disposed in at least a part of the scanning area overlap each other, in a case in which the light quantity detected by the light quantity detector is less than a predetermined quantity. The one or more controllers control the illuminator such that the light source is turned on in a period in which at least parts of the exposure periods of the pixels disposed in at least a part of the scanning area overlap each other, in a case in which the light quantity detected by the light quantity detector is less than the predetermined quantity. The one or more controllers set an exposure time that is a length of the exposure period of the pixels to a second time that is shorter than a first time, in a case in which the light quantity detected by the light quantity detector is equal to or greater than the predetermined quantity. The one or more controllers set the exposure time of the pixels to the first time, in a case in which the light quantity detected by the light quantity detector is less than the predetermined quantity, after the exposure time of the pixels is set to the second time.

According to a second aspect of the present invention, in the first aspect, the light quantity detector may be at least a part of the plurality of the pixels.

According to a third aspect of the present invention, in the first aspect, the light quantity detector may be a device disposed independently from the imaging element.

According to a fourth aspect of the present invention, in the second aspect, the one or more controllers may compare a sum of signal values of the video signals corresponding to the imaging signals read from the pixels constituting the light quantity detector with the predetermined quantity.

According to a fifth aspect of the present invention, in the first aspect, the one or more controllers may set the exposure time of the pixels to the second time corresponding to the light quantity detected by the light quantity detector, in a case in which the light quantity is equal to or greater than the predetermined quantity.

According to a sixth aspect of the present invention, in the first aspect, the one or more controllers may control the imaging element such that at least parts of the exposure periods of the pixels disposed in at least a part of the scanning area overlap each other in a second frame period, in a case in which the light quantity detected by the light quantity detector in a first frame period is less than the predetermined quantity. The first frame period and the second frame period may be continuous frame periods.

According to a seventh aspect of the present invention, in the first aspect, the one or more controllers may control the illuminator such that the light source is turned off, in a case in which the light quantity detected by the light quantity detector is equal to or greater than the predetermined quantity.

According to an eighth aspect of the present invention, in the first aspect, first scanning and second scanning may be executed in a frame period. The one or more controllers may set the scanning area of the first scanning and the scanning area of the second scanning in the imaging element. The light quantity detector may be the pixels disposed in at least one of a plurality of rows. The pixels constituting the light quantity detector may constitute the scanning area of the first scanning The one or more controllers may control the imaging element such that at least parts of the exposure periods of the pixels disposed in at least a part of the scanning area of the second scanning overlap each other, in a case in which the light quantity detected by the light quantity detector is less than the predetermined quantity.

According to a ninth aspect of the present invention, in the eighth aspect, all of the pixels disposed in the imaging area may constitute the scanning area of the second scanning According to a tenth aspect of the present invention, in the eighth aspect, the one or more controllers may set the exposure time of the pixels of the scanning area of the first scanning to a third time. The one or more controllers may set the exposure time of the pixels of the scanning area of the second scanning to the first time that is longer than the third time, in a case in which the light quantity detected by the light quantity detector is less than the predetermined quantity.

According to an eleventh aspect of the present invention, in the ninth aspect, the one or more controllers may control the illuminator such that the light source is turned off in the second scanning, in a case in which the light quantity detected by the light quantity detector is equal to or greater than the predetermined quantity. The one or more controllers may control the imaging element such that the imaging signals are read only from the pixels of a part of columns disposed in the imaging area in the second scanning.

According to a twelfth aspect of the present invention, in the eighth aspect, the one or more controllers may set the exposure time of the pixels of the scanning area of the second scanning to the first time, in a case in which the light quantity detected by the light quantity detector is less than the predetermined quantity. The one or more controllers may set the exposure time of the pixels of the scanning area of the second scanning to the second time, in a case in which the light quantity detected by the light quantity detector is equal to or greater than the predetermined quantity. The one or more controllers may control the illuminator such that the light source is turned off in the second scanning, in a case in which the light quantity detected by the light quantity detector is equal to or greater than the predetermined quantity.

According to a thirteenth aspect of the present invention, a method of operating an endoscope apparatus includes a first step, a second step, a third step, and a fourth step. The endoscope apparatus includes an imaging element, a video signal generating circuit, an illuminator, a light quantity detector, and one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels in each row in the scanning area. The video signal generating circuit generates video signals from the imaging signals. The illuminator includes a light source generating illumination light emitted to the subject. The light quantity detector detects a light quantity at a place in which the imaging element is disposed. The one or more controllers control the imaging element such that at least parts of exposure periods of the pixels disposed in at least a part of the scanning area overlap each other in the first step, in a case in which the light quantity detected by the light quantity detector is less than a predetermined quantity. The one or more controllers control the illuminator such that the light source is turned on in a period in which at least parts of the exposure periods of the pixels disposed in at least a part of the scanning area overlap each other in the second step, in a case in which the light quantity detected by the light quantity detector is less than the predetermined quantity. The one or more controllers set an exposure time that is a length of the exposure period of the pixels to a second time that is shorter than a first time in the third step, in a case in which the light quantity detected by the light quantity detector is equal to or greater than the predetermined quantity. The one or more controllers set the exposure time of the pixels to the first time in the fourth step, in a case in which the light quantity detected by the light quantity detector is less than the predetermined quantity, after the exposure time of the pixels is set to the second time.

According to a fourteenth aspect of the present invention, a non-transitory computer-readable recording medium having a program for causing one or more controllers of an endoscope apparatus to execute a first step, a second step, a third step, and a fourth step recorded thereon is provided. The endoscope apparatus includes an imaging element, a video signal generating circuit, an illuminator, a light quantity detector, and the one or more controllers. The imaging element generates imaging signals by imaging a subject. The imaging element includes a plurality of pixels disposed in a matrix pattern. An imaging area in which the plurality of pixels are disposed includes a scanning area. The imaging signals are read from at least a part of the pixels in each row in the scanning area. The video signal generating circuit generates video signals from the imaging signals. The illuminator includes a light source generating illumination light emitted to the subject. The light quantity detector detects a light quantity at a place in which the imaging element is disposed. The one or more controllers control the imaging element such that at least parts of exposure periods of the pixels disposed in at least a part of the scanning area overlap each other in the first step, in a case in which the light quantity detected by the light quantity detector is less than a predetermined quantity. The one or more controllers control the illuminator such that the light source is turned on in a period in which at least parts of the exposure periods of the pixels disposed in at least a part of the scanning area overlap each other in the second step, in a case in which the light quantity detected by the light quantity detector is less than the predetermined quantity. The one or more controllers set an exposure time that is a length of the exposure period of the pixels to a second time that is shorter than a first time in the third step, in a case in which the light quantity detected by the light quantity detector is equal to or greater than the predetermined quantity. The one or more controllers set the exposure time of the pixels to the first time in the fourth step, in a case in which the light quantity detected by the light quantity detector is less than the predetermined quantity, after the exposure time of the pixels is set to the second time.

DETAILED DESCRIPTION OF THE PREFERRED EMBODIMENT (First Embodiment)

Figure 1:
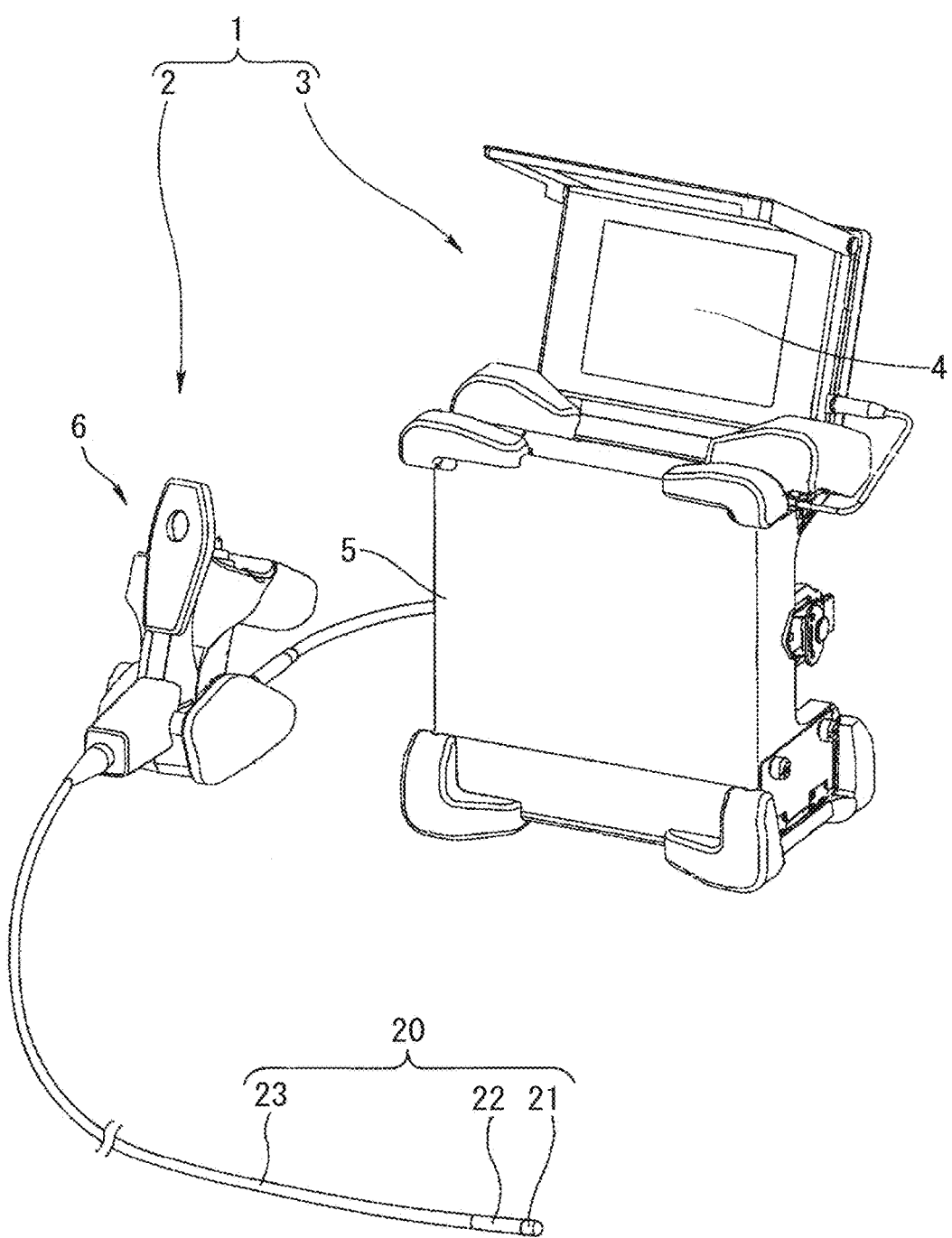
FIG. 1 is a perspective view showing the entire configuration of an endoscope apparatus according to a first embodiment of the present invention.
Figure 2:
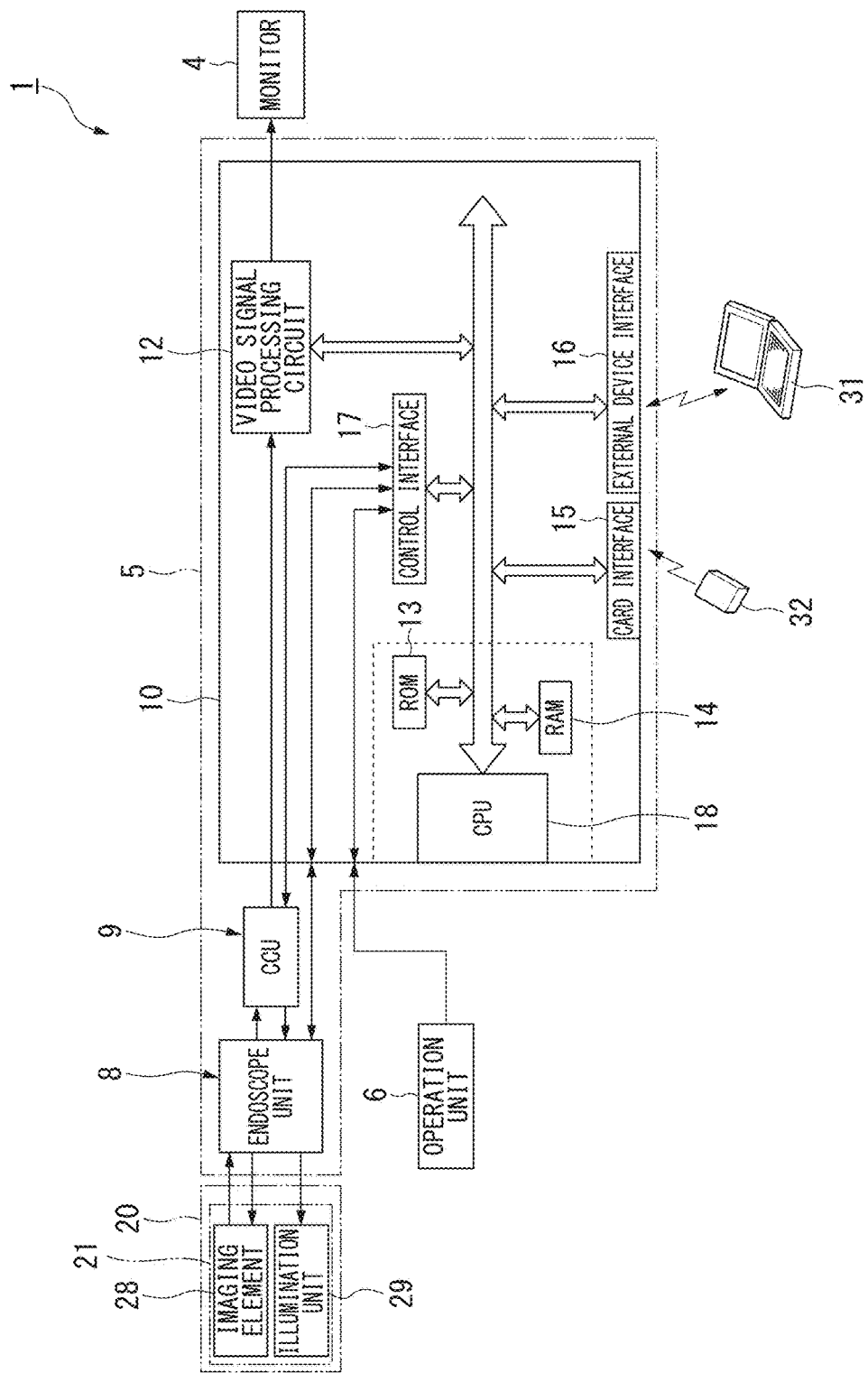
FIG. 2 is a block diagram showing the internal configuration of the endoscope apparatus according to the first embodiment of the present invention.

FIG. 1 shows the entire configuration of an endoscope apparatus 1 according to a first embodiment of the present invention. FIG. 2 shows the internal configuration of the endoscope apparatus 1. As shown in FIG. 1, the endoscope apparatus 1 includes an endoscope 2 and a main body 3. The endoscope 2 includes an elongated insertion unit 20 and an operation unit 6 used for a user to perform a necessary operation for controlling the entire apparatus. The main body 3 is connected to the endoscope 2. The main body 3 includes a monitor 4 and a casing 5. The monitor 4 displays an image of a subject captured by the endoscope 2, an operation menu, and the like. The casing 5 includes a main control unit 10 (see FIG. 2) on the inside thereof.

The insertion unit 20 is inserted into the inside of a test object. The insertion unit 20 includes, a rigid tip end part 21, a bending part 22 that can be bent, and a flexible tube part 23 that has flexibility. The tip end part 21 is disposed on the tip end side of the insertion unit 20. The flexible tube part 23 is disposed on the main body side of the insertion unit 20. The bending part 22 is disposed between the tip end part 21 and the flexible tube part 23. An optical adaptor for forming a subject image can be detachably attached to the tip end part 21.

As shown in FIG. 2, the tip end part 21 includes an imaging element 28 and an illumination unit 29 (illuminator). The imaging element 28 executes photoelectric conversion of a subject image formed through the optical adaptor to generate an imaging signal. For example, the imaging element 28 is a complementary metal oxide semiconductor (CMOS) image sensor. The imaging element 28 includes a plurality of pixels disposed in a matrix pattern. The operations of the plurality of pixels are controlled for each row of the arrangement of the plurality of pixels.

The illumination unit 29 includes a light source that generates illumination light emitted to a subject. For example, the light source is a light emitting diode (LED). The illumination unit 29 may be disposed inside the casing 5, and illumination light generated by the illumination unit 29 may be guided by a light guide to the tip end part 21.

The casing 5 includes an endoscope unit 8, a camera control unit (CCU) 9, and a main control unit 10. The endoscope unit 8 includes a light source driving device that drives the light source of the illumination unit 29 and a bending device that bends the bending part 22. The CCU 9 drives the imaging element 28. An imaging signal output from the imaging element 28 is input to the CCU 9. The CCU 9 executes a pre-process including amplification, noise elimination, and the like for an imaging signal acquired by the imaging element 28. The CCU 9 converts the imaging signal for which the pre-process has been executed into a video signal such as an NTSC signal.

The main control unit 10 includes, a video signal processing circuit 12, a read only memory (ROM) 13, a random access memory (RAM) 14, a card interface 15, an external device interface 16, a control interface 17, and a central processing unit (CPU) 18.

The video signal processing circuit 12 executes predetermined video signal processing for a video signal output from the CCU 9. For example, the video signal processing circuit 12 may compose a video signal output from the CCU 9 and an image of an operation screen or measurement information generated by the CPU 18. The video signal processing circuit 12 outputs the composed video signal to the monitor 4.

The ROM 13 is a nonvolatile recording medium in which a program used for the CPU 18 to control the operation of the endoscope apparatus 1 is recorded. The RAM 14 is a volatile recording medium in which information used by the CPU 18 for controlling the endoscope apparatus 1 is temporarily stored. The CPU 18 controls the operation of the endoscope apparatus 1 on the basis of a program recorded in the ROM 13. The CPU 18 may drive the imaging element 28 not through the CCU 9.

A memory card 32 that is an attachable and detachable recording medium is connected to the card interface 15. The card interface 15 obtains control processing information, image information, and the like stored in the memory card 32 into the main control unit 10. In addition, the card interface 15 records the control processing information, the image information, and the like generated by the endoscope apparatus 1 in the memory card 32.

An external device such as a USB device is connected to the external device interface 16. For example, a personal computer 31 is connected to the external device interface 16. The external device interface 16 transmits information to the personal computer 31 and receives information from the personal computer 31. Accordingly, the monitor of the personal computer 31 can display information. In addition, a user can perform an operation regarding the control of the endoscope apparatus 1 through the personal computer 31.

The control interface 17 communicates with the operation unit 6, the endoscope unit 8, and the CCU 9 for operation control. The control interface 17 notifies the CPU 18 of an instruction input by a user through the operation unit 6. The control interface 17 outputs a control signal used for controlling the illumination unit 29 to the endoscope unit 8. The control interface 17 outputs a control signal used for controlling the imaging element 28 to the CCU 9. In a case in which the CPU 18 controls the imaging element 28 not through the CCU 9, the control interface 17 outputs a control signal used for controlling the imaging element 28 to the imaging element 28.

A program executed by the CPU 18 may be recorded in a computer-readable recording medium. The program recorded in this recording medium may be read by a computer other than the endoscope apparatus 1 and executed. For example, the personal computer 31 may read and execute the program. The personal computer 31 may control the endoscope apparatus 1 by transmitting control information used for controlling the endoscope apparatus 1 to the endoscope apparatus 1 in accordance with a program. Alternatively, the personal computer 31 may acquire a video signal from the endoscope apparatus 1 and execute measurement using the acquired video signal.

The program described above may be transmitted from a computer including a storage device in which this program is stored and the like to the endoscope apparatus 1 through a transmission medium or a transmission wave in a transmission medium. The "transmission medium" transmitting a program is a medium having a function of transmitting information such as a network (communication network) including the Internet or a communication circuit line (communication line) such as a telephone circuit line. In addition, the program described above may realize a part of the functions described above. Furthermore, the program described above may be a differential file (differential program) that can realize the functions described above by being combined with a program that is already recorded in the computer.

Figure 3:
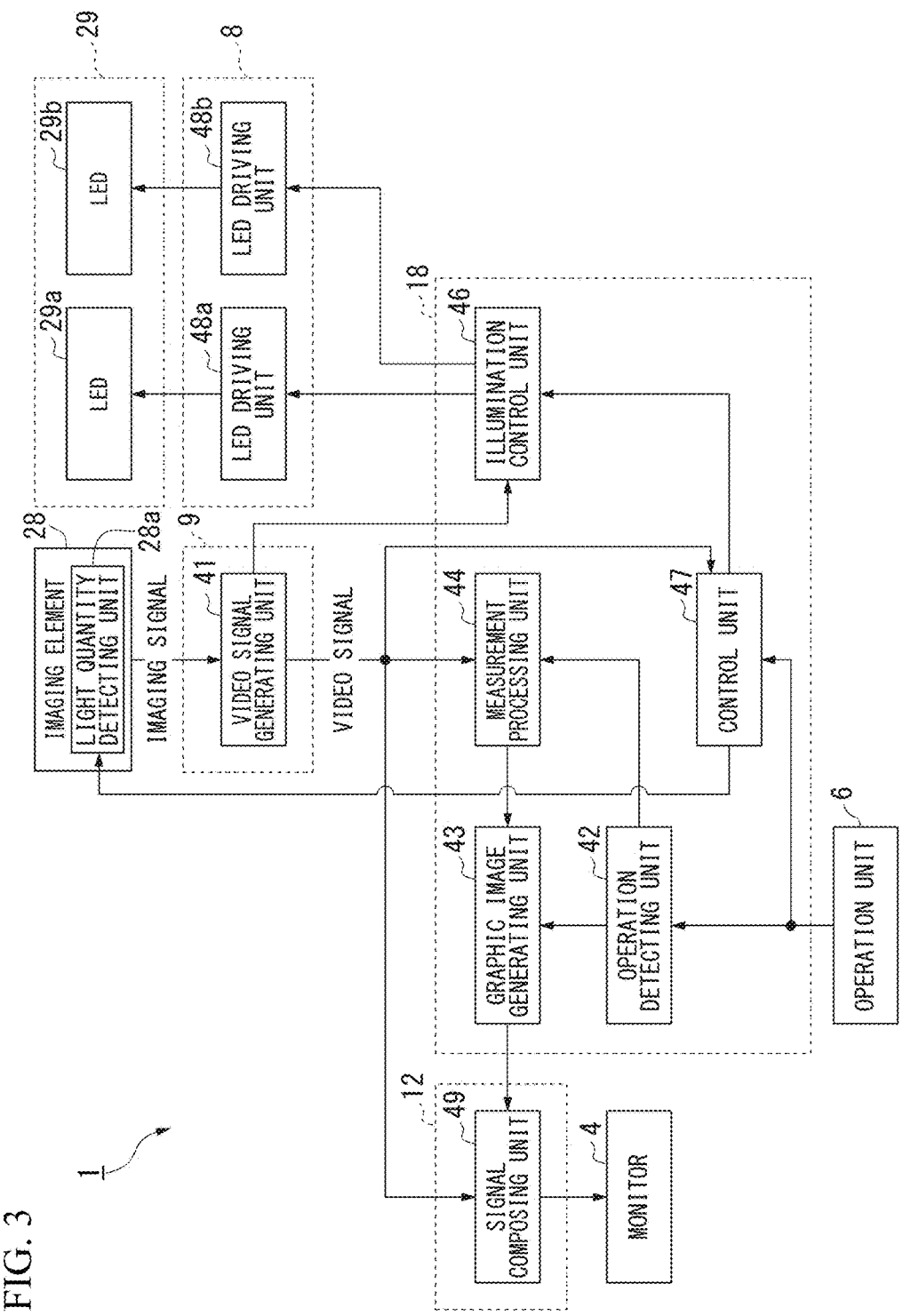
FIG. 3 is a block diagram showing a configuration regarding major functions of the endoscope apparatus according to the first embodiment of the present invention.

FIG. 3 is a block diagram showing a configuration regarding major functions of the endoscope apparatus 1. As shown in FIG. 3, the endoscope apparatus 1 includes a monitor 4 (display), an operation unit 6, an imaging element 28, an LED 29a, an LED 29b, a video signal generating unit 41 (video signal generating circuit), an operation detecting unit 42, a graphic image generating unit 43, a measurement processing unit 44, an illumination control unit 46, a control unit 47, an LED driving unit 48a, an LED driving unit 48b, and a signal composing unit 49.

The imaging element 28 includes a light quantity detecting unit 28a (light quantity detector). The light quantity detecting unit 28a is at least a part of a plurality of pixels included in the imaging element 28. The light quantity detecting unit 28a detects a light quantity at a place (environment) at which the imaging element 28 is disposed. In other words, the light quantity detecting unit 28a detects a light quantity at the surroundings of the imaging element 28 including light from a subject.

The illumination unit 29 includes the LED 29a and the LED 29b that are light sources. The LED 29a is a light source used for observation and stereo measurement. For example, the LED 29b may be a light source used for projecting a pattern onto a subject. In the stereo measurement, a matching process of detecting corresponding positions of two images having parallax is executed. In a case in which there are small features on the surface of a subject, the accuracy of the matching process easily decreases. By projecting a pattern onto a subject, the accuracy of the matching process is improved. The LED 29b may be a light source used for projecting stripes onto a subject. The endoscope apparatus 1 may execute three-dimensional measurement using a phase shift method. In the phase shift method, a pattern formed by parallel stripes is projected onto the surface of a subject. The position of the stripes changes temporally. Three-dimensional measurement is executed on the basis of a change in the luminance of each pixel of a subject image.

The light source of the illumination unit 29 may be a light source other than an LED. The illumination unit 29 may include only one light source or three or more light sources.

The video signal generating unit 41 corresponds to the function of the CCU 9. The video signal generating unit 41 generates a video signal from an imaging signal output from the imaging element 28. The video signal generating unit 41 executes a preprocess including amplification, noise elimination, and the like for the imaging signal and converts the imaging signal into a video signal.

The operation detecting unit 42, the graphic image generating unit 43, the measurement processing unit 44, the illumination control unit 46, and the control unit 47 correspond to functions of the CPU 18. The operation detecting unit 42 detects a user's operation for the operation unit 6. The operation detecting unit 42 sets a display position of a target displayed on the screen of the monitor 4 in accordance with operation details. The target represents the position of a measurement point. A user can move the target in the screen by operating the operation unit 6.

The graphic image generating unit 43 generates a graphic image signal corresponding to an operation menu and measurement information displayed on the screen of the monitor 4. The measurement information includes an image of the target and measurement results. As described above, the display position of the target in the screen is set by the operation detecting unit 42. The measurement processing unit 44 executes a measurement process on the basis of a video signal generated by the video signal generating unit 41. In the measurement process, an object distance, a length, an area, and the like are calculated. The object distance is a distance from the tip end part 21 to a subject.

The illumination control unit 46 outputs a control signal used for controlling the illumination unit 29. In this way, the illumination control unit 46 controls the illumination unit 29. There are many cases in which the inside of a target object for observation or measurement in which the insertion unit 20 is inserted is dark. For this reason, the illumination control unit 46 turns on the illumination unit 29 when a subject is imaged. Before the insertion unit 20 is inserted into a target object, there are cases in which the surroundings of the imaging element 28 are bright. In other words, there are cases in which a target object is disposed at a bright place. Before the insertion unit 20 is inserted into a target object, a user checks whether or not an image is being acquired by the endoscope apparatus 1 by viewing an image displayed in the monitor 4. At this time, the illumination unit 29 does not need to be turned on. In a case in which the surroundings of the imaging element 28 are bright, by turning off the illumination unit 29, the endoscope apparatus 1 can reduce the generation of blown-out-highlights in an image. In addition, the power consumption can be reduced for the endoscope apparatus 1.

The video signal generating unit 41 detects the position of a row in which an imaging signal is read on the basis of an imaging signal output from the imaging element 28. The video signal generating unit 41 notifies the illumination control unit 46 of the position of the row that has been detected. The illumination control unit 46 controls the operation timing of the illumination unit 29 using a timing at the position of the row notified from the video signal generating unit 41 as a reference. The illumination control unit 46 may control the operation timing of the illumination unit 29 using the operation timing of the imaging element 28 determined by the control unit 47 as a reference.

The control unit 47 controls assignment of processes to the operation detecting unit 42, the graphic image generating unit 43, the measurement processing unit 44, and the illumination control unit 46 and controls the overall operation of the endoscope apparatus 1. In addition, the control unit 47 outputs a control signal used for controlling the imaging element 28. This control signal is transmitted to the imaging element 28 through the CCU 9 and the endoscope unit 8. Alternatively, this control signal is directly transmitted to the imaging element 28. In this way, the control unit 47 controls the imaging element 28.

The LED driving unit 48a and the LED driving unit 48b correspond to functions of the endoscope unit 8. The LED driving unit 48a outputs a driving signal used for driving the LED 29a on the basis of a control signal output from the illumination control unit 46. The LED 29a generates illumination light on the basis of a driving signal output from the LED driving unit 48a. The LED driving unit 48b outputs a driving signal used for driving the LED 29b on the basis of a control signal output from the illumination control unit 46. The LED 29b generates illumination light on the basis of a driving signal output from the LED driving unit 48b.

The signal composing unit 49 corresponds to the function of the video signal processing circuit 12. The signal composing unit 49 composes a video signal generated by the video signal generating unit 41 and a graphic image signal generated by the graphic image generating unit 43. The monitor 4 displays an image on the basis of a video signal output from the signal composing unit 49.

The operation detecting unit 42, the graphic image generating unit 43, the measurement processing unit 44, the illumination control unit 46, and the control unit 47 may be constituted as a processor (controller). For example, the processor may be at least one of a CPU, a digital signal processor (DSP), and a graphics processing unit (GPU). The processor may be at least one of an application specific integrated circuit (ASIC) and a field-programmable gate array (FPGA). The operation detecting unit 42, the graphic image generating unit 43, the measurement processing unit 44, the illumination control unit 46, and the control unit 47 may include one or a plurality of processors.

Figure 4:
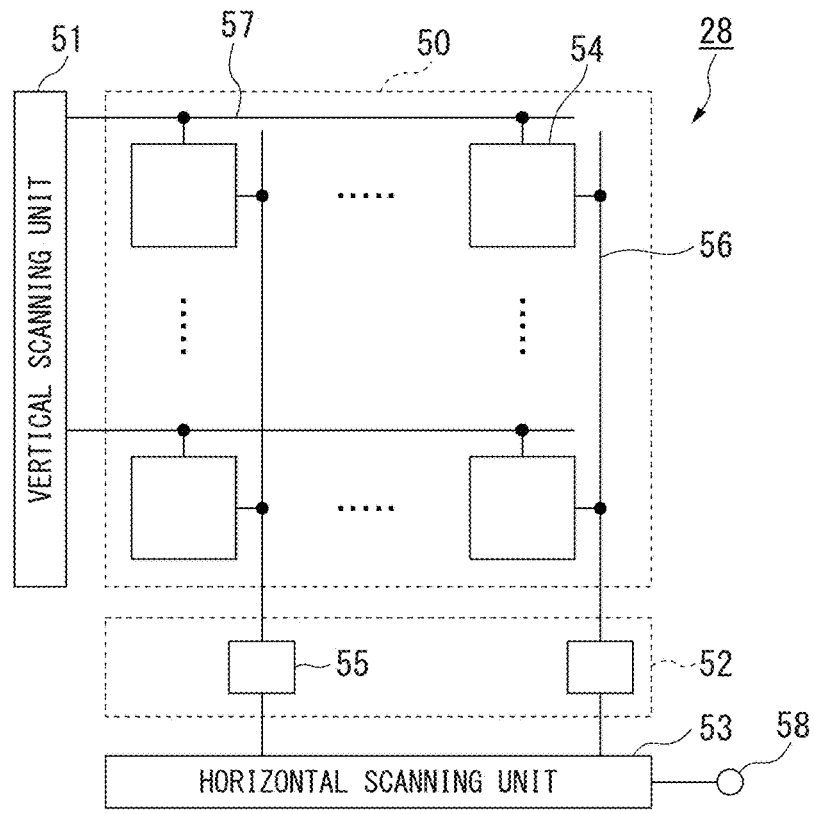
FIG. 4 is a block diagram showing the configuration of an imaging element of the endoscope apparatus according to the first embodiment of the present invention.

FIG. 4 shows the configuration of the imaging element 28. As shown in FIG. 4, the imaging element 28 includes a pixel unit 50, a vertical scanning unit 51, a signal processing unit 52, and a horizontal scanning unit 53.

The pixel unit 50 includes a plurality of pixels 54 disposed in a matrix pattern. The plurality of pixels 54 are disposed in an imaging area of the imaging element 28. Each of the number of rows and the number of columns of the arrangement of the plurality of pixels 54 is two or more. The number of rows and the number of columns need not be the same. Each of the plurality of pixels 54 generates an imaging signal according to the amount of light incident to the pixel 54. Each of the plurality of pixels 54 is connected to a vertical signal line 56. A plurality of vertical signal lines 56 are disposed. Each of the plurality of vertical signal lines 56 is disposed in one column of the arrangement of the plurality of pixels 54. Each of the plurality of pixels 54 outputs a generated imaging signal to the vertical signal line 56.

At least a part of the plurality of pixels 54 constitutes the light quantity detecting unit 28a. The pixels 54 constituting the light quantity detecting unit 28a output results of the detection of light quantities as an imaging signal. The pixels 54 constituting the light quantity detecting unit 28a need not be fixed. For example, the control unit 47 may set an area of pixels 54 constituting the light quantity detecting unit 28a such that a part of pixels 54 disposed in the imaging area or all of the pixels 54 disposed in the imaging area constitutes the light quantity detecting unit 28a.

Each of the plurality of pixels 54 is connected to a control signal line 57. A plurality of control signal lines 57 are disposed. Each of the plurality of control signal lines 57 is disposed for each row of the arrangement of the plurality of pixels 54. Each of the plurality of control signal lines 57 is connected to the vertical scanning unit 51. Control signals used for controlling the operation of the plurality of pixels 54 are output from the vertical scanning unit 51 to the control signal lines 57. A plurality of control signal lines 57 are disposed for the pixels 54 of one row. In FIG. 4, one control signal line 57 is shown for the pixels 54 of one row, and the other control signal lines 57 are not shown. Details of the control signals will be described later.

The operations of the plurality of pixels 54 are controlled on the basis of control signals output to the control signal lines 57. A control signal for the pixels 54 of one row is supplied to be common to all of the pixels 54 in the row. For this reason, the same operation timing is set for two or more pixels 54 disposed in the same row. In other words, two or more pixels 54 disposed in the same row are simultaneously operated. Details of the configuration of the pixels 54 will be described later.

A control signal generated by the control unit 47 is transmitted to the imaging element 28 through the CCU 9 and the endoscope unit 8. Alternatively, a control signal generated by the control unit 47 is directly transmitted to the imaging element 28. The imaging element 28 receives the control signal. The vertical scanning unit 51 generates a control signal used for controlling the operations of the plurality of pixels 54 on the basis of a received control signal. The vertical scanning unit 51 generates a control signal for each of a plurality of rows of the arrangement of the plurality of pixels 54. The vertical scanning unit 51 outputs the generated control signal to the control signal line 57.

The signal processing unit 52 includes a plurality of signal processing circuits 55. The signal processing circuits 55 are disposed for each column of the arrangement of the plurality of pixels 54. The signal processing circuit 55 is connected to the vertical signal line 56. The signal processing circuit 55 executes signal processing including amplification, noise elimination, and the like for an imaging signal output to the vertical signal line 56. At least one of the signal processing circuit 55 and the video signal generating unit 41 (CCU 9) has only to execute signal processing for an imaging signal.

The imaging signal processed by the signal processing circuit 55 is input to the horizontal scanning unit 53. The horizontal scanning unit 53 sequentially selects columns of the arrangement of the plurality of pixels 54. An imaging signal for a column selected by the horizontal scanning unit 53 is output from an output terminal 58.

As described above, the endoscope apparatus 1 includes the imaging element 28, the video signal generating unit 41, the illumination unit 29, the light quantity detecting unit 28a, the control unit 47, and the illumination control unit 46. The imaging element 28 images a subject to generate an imaging signal. The video signal generating unit 41 generates a video signal from the imaging signal. The illumination unit 29 includes light sources (the LED 29a and the LED 29b) generating illumination light emitted to a subject. The light quantity detecting unit 28a detects a light quantity of a place at which the imaging element 28 is disposed. The control unit 47 controls the imaging element 28. The illumination control unit 46 controls the illumination unit 29.

The imaging element 28 includes a plurality of pixels 54 disposed in a matrix pattern. An imaging area in which the plurality of pixels 54 are disposed includes a scanning area. Imaging signals are read from at least a part of pixels 54 of each row in the scanning area. In a case in which a light quantity detected by the light quantity detecting unit 28a is less than a predetermined quantity, the control unit 47 controls the imaging element 28 such that at least parts of exposure periods of pixels 54 disposed in at least a part of the scanning area overlap each other. In a case in which a light quantity detected by the light quantity detecting unit 28a is less than the predetermined quantity, the illumination control unit 46 controls the illumination unit 29 such that the light source is turned on in a period in which at least parts of the exposure periods of pixels 54 disposed in at least a part of the scanning area overlap each other. Details of the control of the scanning area, the imaging element 28, and the illumination unit 29 will be described later.

Figure 5:
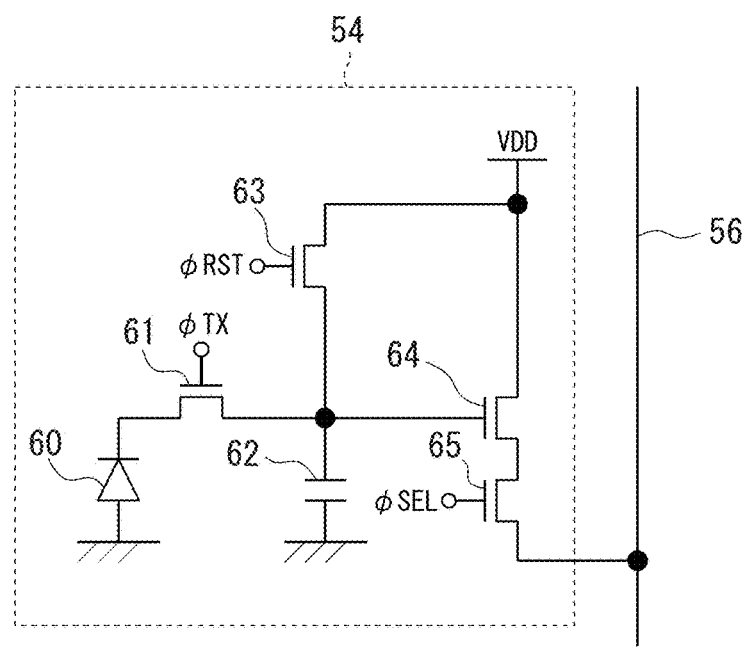
FIG. 5 is a circuit diagram showing the configuration of a pixel of the endoscope apparatus according to the first embodiment of the present invention.

FIG. 5 shows the configuration of the pixel 54. As shown in FIG. 5, the pixel 54 includes a photoelectric conversion unit 60, an electric charge transmitting unit 61, an electric charge accumulating unit 62, a resetting unit 63, an amplification unit 64, and an output unit 65. The photoelectric conversion unit 60 is a photo diode. The electric charge accumulating unit 62 is a capacitor. For example, the electric charge accumulating unit 62 may be the capacitance of the gate of a transistor constituting the amplification unit 64. The electric charge transmitting unit 61, the resetting unit 63, the amplification unit 64, and the output unit 65 are transistors.

The photoelectric conversion unit 60 generates electric charge according to the amount of light incident to the pixel 54. The electric charge transmitting unit 61 transmits electric charge generated by the photoelectric conversion unit 60 to the electric charge accumulating unit 62. The electric charge accumulating unit 62 accumulates electric charge transmitted from the photoelectric conversion unit 60. The resetting unit 63 resets electric charge in the photoelectric conversion unit 60 and the electric charge accumulating unit 62 on the basis of a power source voltage VDD. By turning on the electric charge transmitting unit 61 and the resetting unit 63, the resetting unit 63 can reset the electric charge in the photoelectric conversion unit 60 and the electric charge accumulating unit 62. The amplification unit 64 amplifies a signal based on electric charge accumulated in the electric charge accumulating unit 62. The output unit 65 outputs the signal amplified by the amplification unit 64 to the vertical signal line 56 as an imaging signal.

The operation of the electric charge transmitting unit 61 is controlled using a control signal φTX. The operation of the resetting unit 63 is controlled using a control signal φRST. The operation of the output unit 65 is controlled using a control signal φSEL. The control signal φTX, the control signal φRST, and the control signal φSEL are supplied from the vertical scanning unit 51 through the control signal lines 57.

The operation of the pixel 54 includes resetting, transmission of electric charge, and signal reading. The resetting corresponds to the operation of the resetting unit 63. The transmission of electric charge corresponds to the operation of the electric charge transmitting unit 61. The signal reading corresponds to the operation of the output unit 65.

A measurement process executed by the measurement processing unit 44 will be described. For example, the measurement processing unit 44 executes a measurement process based on the principle of stereo measurement. In the stereo measurement, an optical adapter forming a first optical image and a second optical image having parallax therebetween is used. The imaging element 28 generates an imaging signal based on the first optical image and the second optical image. The monitor 4 displays a first image corresponding to the first optical image and a second image corresponding to the second optical image. For example, the monitor 4 displays an image in which the first image and the second image are horizontally aligned.

A user operates a target on the screen of the monitor 4 through the operation unit 6, thereby designating a measurement point for one of the first image and the second image. For example, a measurement point is designated for the first image. The measurement processing unit 44 processes a video signal, thereby retrieving a corresponding point of the second image that corresponds to the measurement point of the first image. In other words, the measurement processing unit 44 retrieves a corresponding point through pattern matching between the first image and the second image. The measurement processing unit 44 calculates three-dimensional coordinates corresponding to the measurement point on the basis of the principle of triangulation using the measurement point and the corresponding point.

In the stereo measurement, the first optical image and the second optical image are formed in the imaging element 28 simultaneously or alternately. For example, in a case in which the first optical image and the second optical image are alternately formed in the imaging element 28, one of a first optical path and a second optical path is shielded by a movable mechanical shutter. The first optical path is an optical path used for forming the first optical image. The second optical path is an optical path used for forming the second optical image. In a case in which the mechanical shutter is disposed in the second optical path, the first optical image is formed in the imaging element 28. In a case in which the mechanical shutter is disposed in the first optical path, the second optical image is formed in the imaging element 28.

In the stereo measurement, by projecting a pattern onto a subject, the accuracy of the matching process is improved. For this reason, in the stereo measurement, a pattern may be projected on a subject. The measurement processing unit 44 may execute a process of three-dimensional measurement other than the stereo measurement. For example, the measurement processing unit 44 may execute a measurement process based on the principle of a phase shift method.

As shown in FIG. 3, the illumination unit 29 includes a plurality of independent light sources (the LED 29a and the LED 29b). The illumination control unit 46 selects a light source that generates illumination light.

The illumination unit 29 includes a plurality of light sources (the LED 29a and the LED 29b) including a measurement light source (the LED 29b) used for projecting a pattern or stripes on a subject. The endoscope apparatus 1 includes a measurement processing unit 44 that executes a measurement process on the basis of a video signal. In a case in which the measurement processing unit 44 executes the measurement process, the illumination control unit 46 may turn on the measurement light source.

For example, in a case in which the endoscope apparatus 1 generates a video signal by continuously imaging a subject and the image of the subject is displayed, the illumination control unit 46 selects the LED 29a. In a case in which general stereo measurement is executed, the illumination control unit 46 selects the LED 29a. In a case in which the measurement process is executed, and a pattern or stripes are projected onto a subject, the illumination control unit 46 selects the LED 29b.

Figure 6:
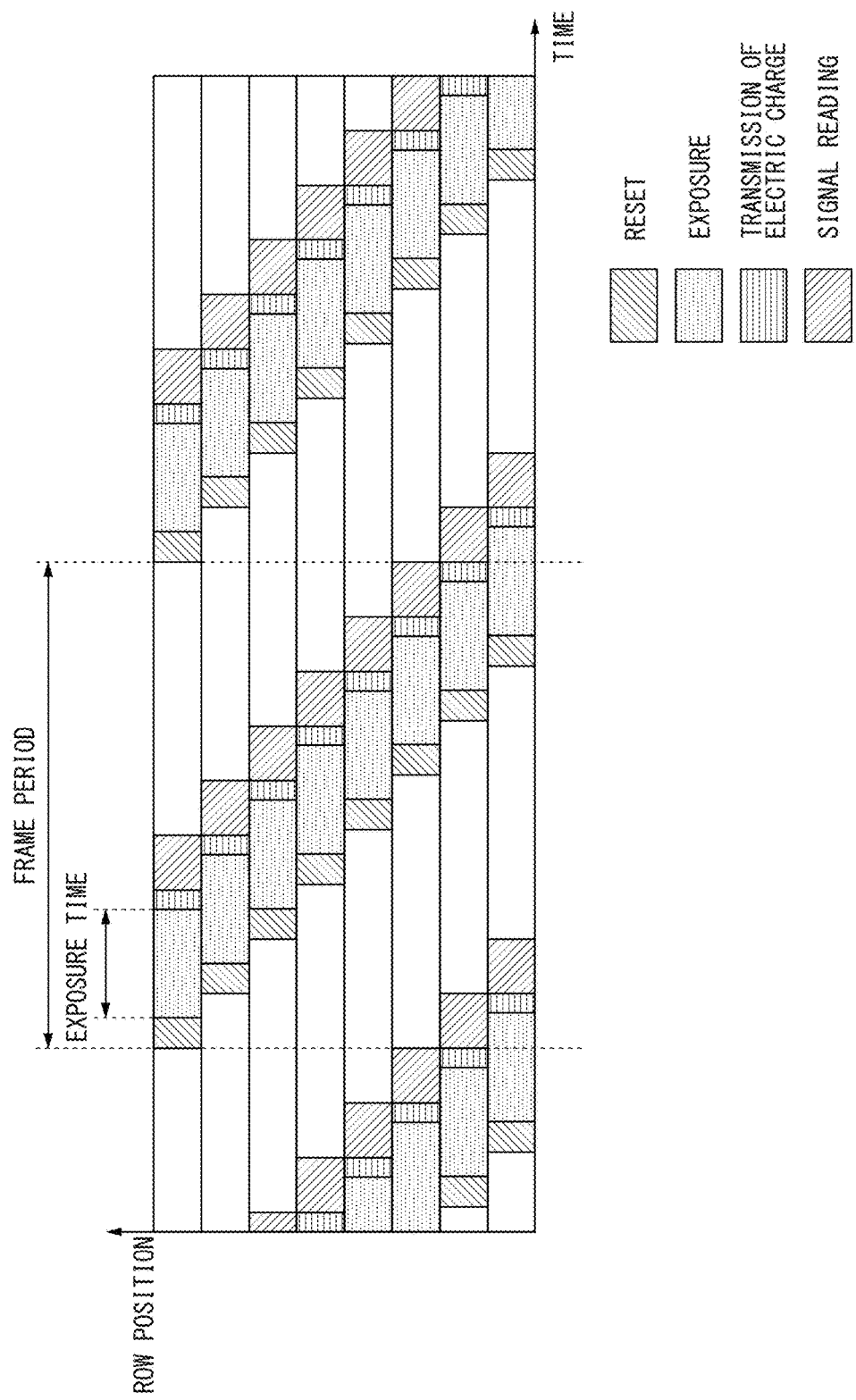
FIG. 6 is a timing chart showing the operation of the endoscope apparatus according to the first embodiment of the present invention.

The operation of the endoscope apparatus 1 will be described. FIG. 6 shows an operation executed in a case in which the imaging element 28 is driven by a rolling shutter. In FIG. 6, the horizontal direction represents the time, and the vertical direction represents the row position. FIG. 6 shows an operation of pixels 54 of eight rows. The uppermost row is the first row, and the lowermost row is the eighth row. For example, in the operation shown in FIG. 6, the light source of the illumination unit 29 is continuously controlled to be turned on.

When a frame period based on a display period of the monitor 4 starts, resetting is executed in the pixel 54 of the first row. In other words, in the pixels 54 of the first row, the resetting unit 63 resets electric charge in the photoelectric conversion unit 60 and the electric charge accumulating unit 62. Accordingly, exposure starts in the pixels 54 of the first row. After resetting, transmission of electric charge is executed in the pixels 54 of the first row. In other words, in the pixels 54 of the first row, the electric charge transmitting unit 61 transmits electric charge generated by the photoelectric conversion unit 60 to the electric charge accumulating unit 62. In this way, the exposure in the pixels 54 of the first row ends. A period from exposure start to exposure end is an exposure period (exposure possible period). In other words, the exposure period is a period from the end of resetting to the start of transmission of electric charge. After the transmission of electric charge, signal reading is executed in the pixels 54 of the first row. In other words, in the pixels 54 of the first row, the output unit 65 outputs an imaging signal to the vertical signal line 56. After signal reading is executed, the pixels 54 of the first row wait until the next frame period starts.

At a timing at which a predetermined time elapses from a timing at which resetting is executed in the pixels 54 of the first row, resetting is executed in the pixels 54 of the second row. An operation executed in the pixels 54 of the second row is similar to that executed in the pixels 54 of the first row. The operation in the pixels 54 of the second row is executed at a timing shifted from the timing of the operation executed in the pixels 54 of the first row by a predetermined time. Similarly, an operation in the pixels 54 of each of rows that are the third row and subsequent rows is executed at a timing shifted from the timing of the operation executed in the pixels 54 of the previous row by a predetermined time.

Figure 7:
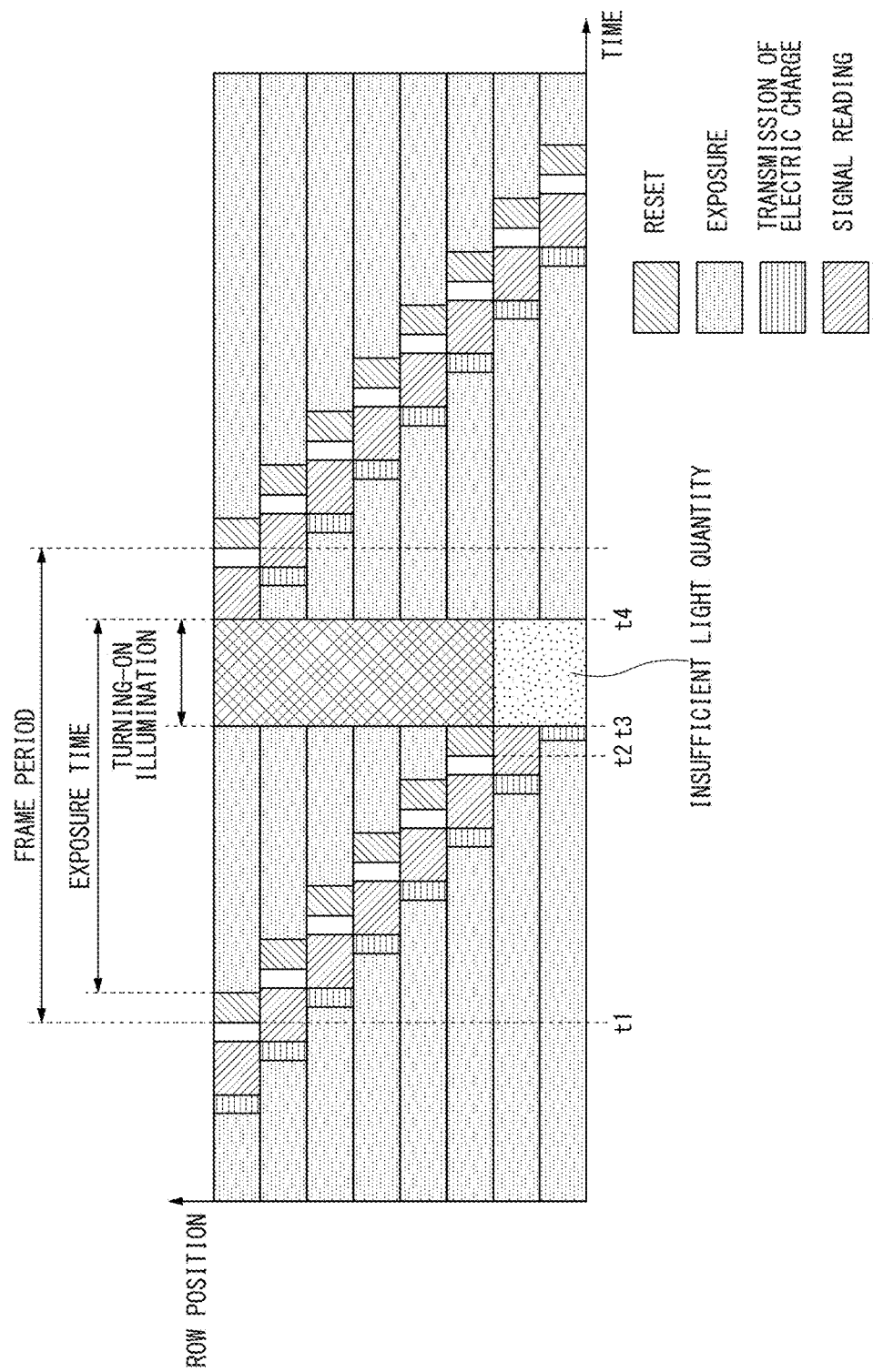
FIG. 7 is a timing chart showing the operation of the endoscope apparatus according to the first embodiment of the present invention.

FIG. 7 shows a featured operation of the endoscope apparatus 1. In FIG. 7, the horizontal direction represents the time, and the vertical direction represents the row position. FIG. 7 shows an operation of pixels 54 of eight rows. The uppermost row is the first row, and the lowermost row is the eighth row.

In the operation shown in FIG. 7, the imaging element 28 is driven by a rolling shutter. Exposure periods are set such that at least parts of the exposure periods of the pixels 54 of two or more rows overlap each other. In the operation shown in FIG. 7, exposure periods are set such that at least parts of the exposure periods of the pixels 54 of the first row to the eighth row overlap each other. The illumination control unit 46 controls the illumination unit 29 such that the light source of the illumination unit 29 is intermittently turned on.

At a timing t1 at which resetting starts in the pixels 54 of the first row, the light source of the illumination unit 29 is turned off. At a timing t3 at which signal reading in the pixels 54 of the sixth row ends, the light source of the illumination unit 29 becomes turned on. For example, a timing t2 at which imaging signals of the pixels 54 of the sixth row are output is notified from the video signal generating unit 41 to the illumination control unit 46. The illumination control unit 46 calculates the timing t3 on the basis of the timing t2. The illumination control unit 46 turns on the light source of the illumination unit 29 at the calculated timing t3. At a timing t4 at which signal reading starts in the pixels 54 of the first row, the light source of the illumination unit 29 becomes turned off. For example, the illumination control unit 46 calculates the timing t4 on the basis of the timing t3. The illumination control unit 46 turns off the light source of the illumination unit 29 at the calculated timing t4.

As described above, in the period from the timing t3 to the timing t4 during which the pixels 54 of the first row to the sixth row are simultaneously exposed, the light source of the illumination unit 29 is turned on. In a case in which the surroundings of the tip end part 21 are dark, most of light incident to the plurality of pixels 54 is based on the light of only light sources of the illumination unit 29 that are turned on from the timing t3 to the timing t4. For this reason, in the pixels 54 of the first row to the sixth row of the imaging element 28 driven by a rolling shutter, a subject image based on light that is simultaneously incident to the pixels 54 is captured. Accordingly, in the image based on the imaging signals output from the pixels 54 from the first row to the sixth row, distortion of the subject is decreased.

A period other than the exposure period in the pixels 54 of the seventh row and the eighth row is included in a period from the timing t3 to the timing t4. In other words, a length of a period in which the pixels 54 of the seventh row and the eighth row are exposed is shorter than a length of a period in which the pixels 54 of the first row to the sixth row are exposed. For this reason, in the pixels 54 of the seventh row and the eighth row, compared to the pixels 54 of the first row to the sixth row, the exposure amount is insufficient.

The control unit 47 controls at least one of a scanning rate, a scanning area, a scanning start timing, an exposure time, and a gain.

The scanning rate is a scanning speed of the plurality of pixels 54. A difference in the operation timings of pixels 54 of each row disposed in the imaging element 28 driven by a rolling shutter is based on the scanning rate. An imaging signal is read from the pixels 54 of each row at a timing based on the scanning rate.

The scanning area includes all or some of the plurality of pixels 54 disposed in the imaging area of the imaging element 28. The scanning area includes all of the pixels 54 in which at least resetting and transmission of electric charge are executed and includes at least all of the pixels 54 in which signal reading is executed. The scanning area may include pixels 54 in which resetting and transmission of electric charge are executed, and signal reading is not executed. In the scanning area, all of the rows include one or more pixels 54 from which imaging signals are read. Imaging signals are read from all or some of the pixels 54 disposed in the scanning area. For example, block reading in which imaging signals are read only from pixels 54 disposed in parts of all of the columns may be executed. The control unit 47 may control an area in which block reading is executed in the scanning area.

In the operation shown in FIG. 7, the pixels 54 of the first row to the eighth row are included in the scanning area. In a case in which the light source of the illumination unit 29 is turned on from the timing t3 to the timing t4, only the pixels 54 of the first row to the sixth row may be included in the scanning area. The control unit 47 controls the imaging element 28 such that imaging signals are output only from the pixels 54 of the scanning area. In a case in which the scanning area is set only in a part of the imaging area, the processing load of the CPU 18 required for reading imaging signals is decreased. For this reason, the endoscope apparatus 1 can execute generation of imaging signals and the measurement process in one frame period. In other words, the endoscope apparatus 1 can execute the measurement process in real time in synchronization with continuous imaging operations.

A scanning start timing is a timing at which the scanning of the plurality of pixels 54 starts. The scanning start timing represents a start timing of the operations of the plurality of pixels 54 in the frame period. In a case in which the pixels 54 of the rows are sequentially scanned from the pixels 54 of the first row, the scanning start timing represents a start timing of the operations of the pixels 54 of the first row. For example, the scanning start timing represents a timing at which resetting starts in the pixels 54 of the first row.

An exposure time is the length of the exposure period. In other words, the exposure time is a length of a period from the timing of the end of resetting to the timing of the start of transmission of electric charge. The exposure time in the operation shown in FIG. 7 may be longer than the exposure time in the operation shown in FIG. 6. As the exposure time is increased, the exposure periods of the pixels 54 of more rows can easily overlap each other.

A gain is a gain of amplification in the video signal generating unit 41 or the signal processing unit 52. A different gain may be set for each row of the arrangement of the plurality of pixels 54.

The illumination control unit 46 controls at least one of a turning-on timing, a turning-on time, and a light quantity.

A turning-on timing is a timing at which the light source of the illumination unit 29 starts to be turned on. A turning-on time is time in which the light source of the illumination unit 29 continues to be turned on. In other words, the turning-on time is time from a turning-on start timing (turning-on timing) to a turning-on end timing (turning-off timing). In a case in which the light source of the illumination unit 29 is intermittently turned on, the turning-on time is shorter than the exposure time. A light quantity is the light quantity of the light source of the illumination unit 29. In the operation shown in FIG. 7, the illumination control unit 46 controls the illumination unit 29 such that the light source of the illumination unit 29 is turned on in a period in which at least parts of the exposure periods of the pixels 54 of the first row to the eighth row included in the scanning area overlap each other.

In a case in which the light quantity is less than a predetermined quantity, and the measurement process is executed by the measurement processing unit 44, the control unit 47 may control the imaging element 28 such that at least parts of the exposure periods of pixels 54 disposed in at least a part of the scanning area overlap each other. In a case in which the light quantity is less than a predetermined quantity, and the measurement process is executed by the measurement processing unit 44, the illumination control unit 46 may control the illumination unit 29 such that the light source is turned on in a period in which at least parts of the exposure periods of pixels 54 disposed in at least a part of the scanning area overlap each other. In this way, the endoscope apparatus 1 can execute the measurement process on the basis of an image in which the distortion of the subject is decreased. In other words, the measurement accuracy is improved.

Figure 8:
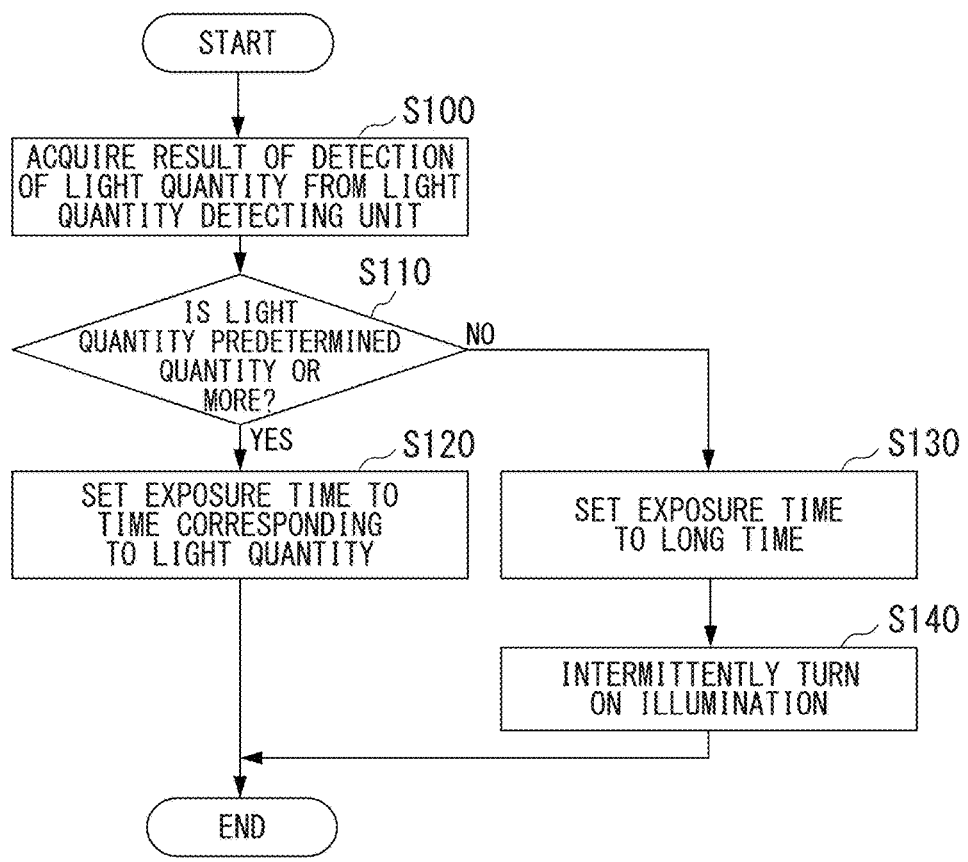
FIG. 8 is a flowchart showing the procedure of the operation of the endoscope apparatus according to the first embodiment of the present invention.

The operation of the endoscope apparatus 1 regarding the control of the imaging element 28 and the illumination unit 29 will be described. FIG. 8 shows the procedure of the operation of the endoscope apparatus 1 regarding the control of the imaging element 28 and the illumination unit 29. The control unit 47 acquires a result of the detection of a light quantity (Step S100). In Step S100, the control unit 47 acquires a video signal as a result of the detection of the light quantity. The video signal generated from imaging signals output from the pixels 54 constituting the light quantity detecting unit 28a represents the result of the detection of the light quantity.

After Step S100, the control unit 47 determines whether or not the detected light quantity is equal to or greater than a predetermined quantity (Step S110). In Step S110, the control unit 47 determines whether or not the signal value of the video signal generated from the imaging signals output from the pixels 54 constituting the light quantity detecting unit 28a is equal to or greater than a predetermined quantity. For example, in Step S110, the control unit 47 compares a sum of signal values of video signals corresponding to the imaging signals read from the pixels 54 constituting the light quantity detecting unit 28a with a predetermined quantity.

In Step S110, in a case in which the light quantity is determined to be equal to or greater than the predetermined quantity, the control unit 47 sets an exposure time according to the light quantity (Step S120). In a case in which the light quantity is equal to or greater than a predetermined quantity, and the light quantity is larger, the exposure time is set to a shorter time. In a case in which the light quantity is large, by setting the exposure time to be shorter than the exposure time of a case in which the light quantity is small, the endoscope apparatus 1 can reduce the generation of blown-out-highlights in the image. The exposure time set in Step S120 is equal to or less than a predetermined time for the predetermined light quantity.

In Step S110, in a case in which the light quantity is determined to be less than the predetermined quantity, the control unit 47 sets the exposure time to a long time (Step S130). The exposure time set in Step S130 is longer than a longest exposure time that can be set in Step S120. By increasing the exposure time, the endoscope apparatus 1 can set exposure periods such that the exposure periods of the pixels 54 of more rows overlap each other.

After Step S130, the illumination control unit 46 intermittently turns on the light source of the illumination unit 29 in a period in which at least parts of the exposure periods of all of the pixels 54 disposed in the scanning area overlap each other (Step S140). In a case in which the light quantity is small, by intermittently turning on the light source of the illumination unit 29, the endoscope apparatus 1 can acquire an image in which the distortion of the subject is reduced.

In a case in which the imaging element 28 continuously images the subject, the endoscope apparatus 1 repeatedly executes the process shown in FIG. 8.

For example, in the process shown in FIG. 8, the entire imaging area is the scanning area. Different scanning areas may be set between a case in which the light quantity is equal to or greater than the predetermined quantity and a case in which the light quantity is less than the predetermined quantity. In a case in which the light quantity is equal to or greater than the predetermined quantity, the entire imaging area may be set as the scanning area. On the other hand, in a case in which the light quantity is less than the predetermined quantity, a part of the imaging area may be set as the scanning area.

The operation of the endoscope apparatus 1 will be described. Hereinafter, an example of the operation of the endoscope apparatus 1 in a case in which the imaging element 28 continuously images a subject will be shown.

Figure 9:
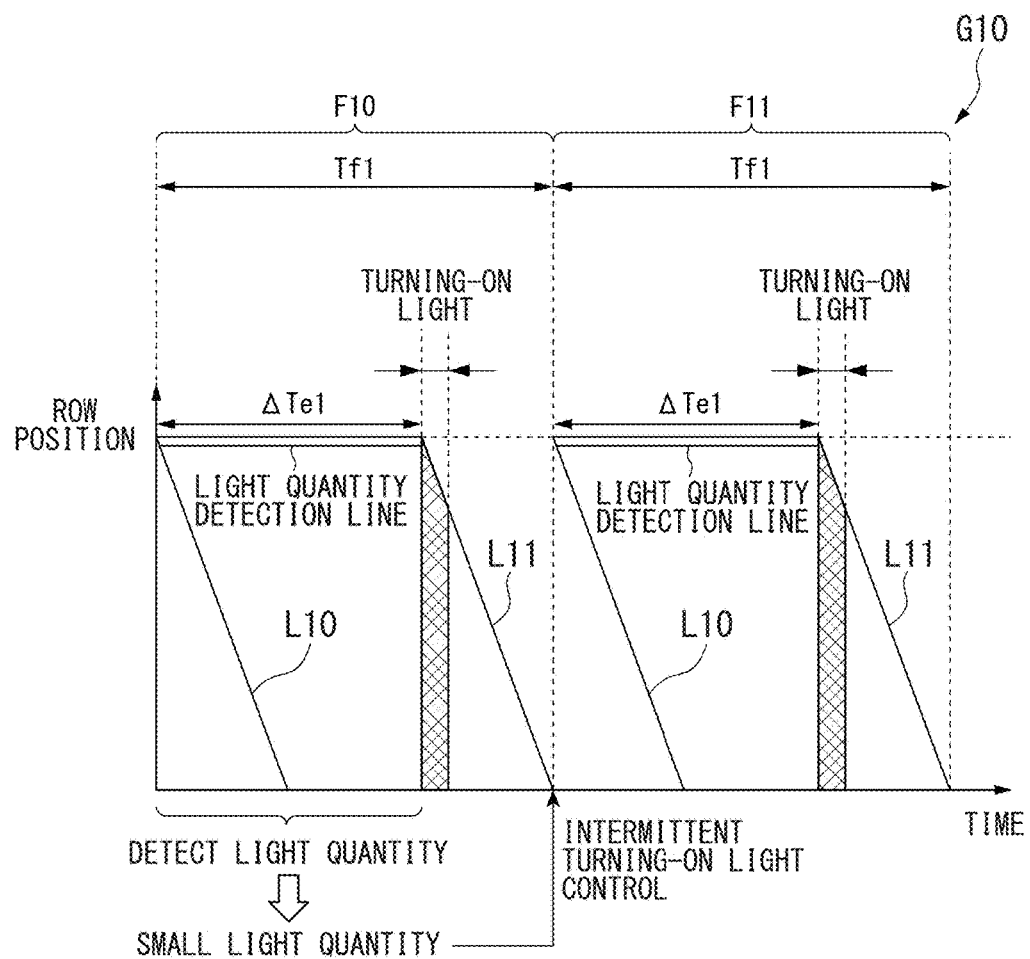
FIG. 9 is a timing chart showing the operation of the endoscope apparatus according to the first embodiment of the present invention.

FIG. 9 shows a first operation of the endoscope apparatus 1. In the following description, the number of vertical pixels of the imaging area, in other words, the number of rows is V. In FIG. 9, a graph G10 shows the timing of the operation of each pixel 54 in the imaging area. In the graph G10, the horizontal direction represents the time, and the vertical direction represents the row position. The uppermost row is the first row, and the lowermost row is the V-th row. The length of the frame period, in other words, the display period of the monitor 4 is Tf1. A frame rate for displaying a live image is 1/Tf1.

The control of the imaging element 28 and the illumination unit 29 is executed for every frame period. In FIG. 9, operations in a frame period F10 and a frame period F11 among a plurality of continuous frame periods are shown. The control of the imaging element 28 and the illumination unit 29 in each frame period is based on a result of the detection of the light quantity in the previous frame period. When each frame period starts, the LED 29a is turned off.

In each frame period, the control unit 47 sets all of the pixels 54 disposed in the imaging area as the scanning area. In the pixels 54 of all of the rows disposed in the imaging area, resetting, transmission of electric charge, and signal reading are executed. By using block reading, signal reading may be executed only in the pixels 54 of a part of the columns disposed in the imaging area. In other words, resetting and transmission of electric charge are executed in the pixels 54 of all of the rows disposed in the imaging area, and signal reading may be executed in only pixels 54 of a part of the columns disposed in the imaging area.

In a case in which the light quantity is less than a predetermined quantity in the previous frame period of a frame period F10, in the frame period F10, the control unit 47 determines a light quantity on the basis of video signals generated from imaging signals output from pixels 54 of the first row (light quantity detection line). In other words, the pixels 54 of the first row constitute the light quantity detecting unit 28a. On the basis of a result of the determination of the light quantity in the frame period F10, the operation executed in a frame period F11 is determined.

In a case in which the light quantity is less than a predetermined quantity in the previous frame period of the frame period F10, in the frame period F10, the LED 29a is controlled to be intermittently turned on. A straight line L10 represents an end timing of resetting in the pixel 54 of each row disposed in the imaging area, in other words, a start timing of exposure. A straight line L11 represents a start timing of transmission of electric charge in the pixels 54 of each row disposed in the imaging area, in other words, an end timing of exposure. The slope of the straight line L10 and the straight line L11 is based on the scanning rate. An exposure period is a period from a timing represented by the straight line L10 to a timing represented by the straight line L11. The length of the exposure period, in other words, the exposure time is $\Delta Te1$.

The illumination control unit 46 intermittently turns on the LED 29a in a period in which at least parts of the exposure periods of all of the pixels 54 except for the pixels 54 of the first row in the imaging area overlap each other. In other words, the illumination control unit 46 intermittently turns on the LED 29a in a period in which at least parts of the exposure periods of all of the pixels 54 except for the pixels 54 constituting the light quantity detecting unit 28a in the imaging area overlap each other. By intermittently turning on the LED 29b, a pattern may be projected onto the subject.

In an operation shown in a graph G10, the LED 29a starts to be turned on at a timing at which the exposure of the pixels 54 of the first row ends. In the exposure periods of pixels 54 of a part of rows, time in which illumination light is emitted to the subject is shorter than the turning-on time of the LED 29a. The video signal generating unit 41 may generate video signals by amplifying imaging signals output from the pixels 54 with a predetermined gain. Alternatively, the signal processing unit 52 may amplify the imaging signals output from the pixels 54 with a predetermined gain. Here, the predetermined gain may be a value according to a ratio of time in which illumination light is emitted to the subject in the exposure period to the turning-on time of the LED 29a.

In a case in which a light quantity is less than a predetermined quantity in the frame period F10, the control of the imaging element 28 and the illumination unit 29 in the frame period F11 is similar to the control in the frame period F10. In a case in which a light quantity in each frame period is less than a predetermined quantity, the operation in which LED 29a is intermittently turned on continues in a plurality of frame periods.

In a case in which the light quantity is less than the predetermined quantity, pixels 54 of two or more rows and less than V rows may constitute the light quantity detecting unit 28a.

Figure 10:
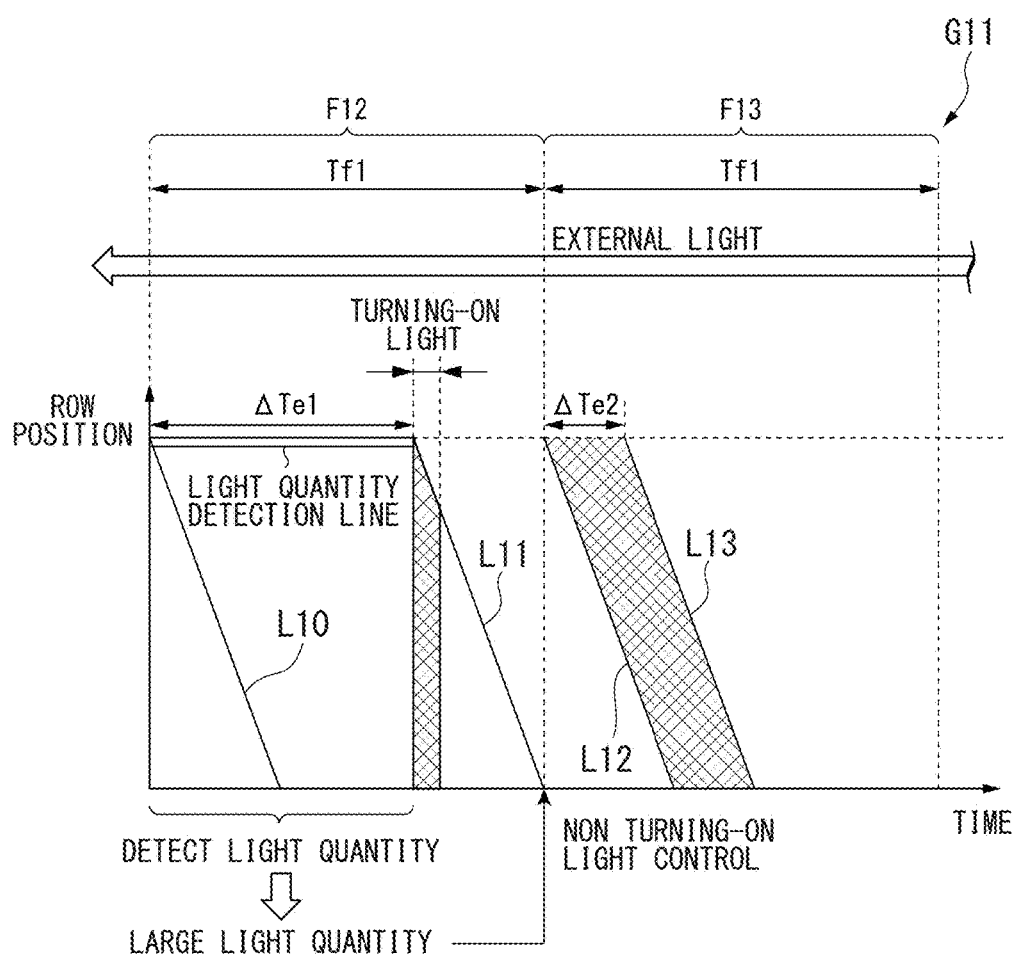
FIG. 10 is a timing chart showing the operation of the endoscope apparatus according to the first embodiment of the present invention.

FIG. 10 shows a second operation of the endoscope apparatus 1. In FIG. 10, a graph G11 shows a timing of the operation of each pixel 54 in an imaging area. In the graph G11, the horizontal direction represents the time, and the vertical direction represents the row position. The uppermost row is the first row, and the lowermost row is the V-th row. The length of the frame period, in other words, the display period of the monitor 4 is Tf1. A frame rate for displaying a live image is 1/Tf1.

The control of the imaging element 28 and the illumination unit 29 is executed for every frame period. In FIG. 10, operations in a frame period F12 and a frame period F13 among a plurality of continuous frame periods are shown. The control of the imaging element 28 and the illumination unit 29 in each frame period is based on a result of the detection of the light quantity in the previous frame period. When each frame period starts, the LED 29a is turned off.

In each frame period, the control unit 47 sets all of the pixels 54 disposed in the imaging area as the scanning area. In the pixels 54 of all of the rows disposed in the imaging area, resetting, transmission of electric charge, and signal reading are executed. By using block reading, signal reading may be executed only in the pixels 54 of a part of the columns disposed in the imaging area. In other words, resetting and transmission of electric charge are executed in the pixels 54 of all of the rows disposed in the imaging area, and signal reading may be executed in only pixels 54 of a part of the columns disposed in the imaging area.

The control of the imaging element 28 and the illumination unit 29 in the frame period F12 is similar to the control in the frame period F10. In a case in which a light quantity in the frame period F12 is equal to or greater than a predetermined quantity, in the frame period F13, the LED 29a is controlled to continue to be in the tuning-off state. A straight line L12 represents an end timing of resetting in the pixel 54 of each row disposed in the imaging area, in other words, a start timing of exposure. A straight line L13 represents a start timing of transmission of electric charge in the pixels 54 of each row disposed in the imaging area, in other words, an end timing of exposure. The slope of the straight line L12 and the straight line L13 is based on the scanning rate. The slope of the straight line L12 and the straight line L13 is the same as the slope of the straight line L10 and the straight line L11. An exposure period is a period from a timing represented by the straight line L12 to a timing represented by the straight line L13. The length of the exposure period, in other words, the exposure time is $\Delta Te2$. The exposure time $\Delta Te2$ is shorter than the exposure time $\Delta Te1$. The exposure time $\Delta Te2$ may be longer than the exposure time $\Delta Te1$. The exposure time $\Delta Te2$ may be the same as the exposure time $\Delta Te1$.

In the frame period F13, the control unit 47 determines a light quantity on the basis of video signals generated from imaging signals output from all of the pixels 54 disposed in the imaging area. In other words, all of the pixels 54 disposed in the imaging area constitute the light quantity detecting unit 28a. On the basis of a result of the determination of the light quantity in the frame period F13, the operation executed in the next frame period of the frame period F13 is determined.

In a case in which a light quantity in the frame period F13 is equal to or greater than a predetermined quantity, in the next frame period of the frame period F13, the control of the imaging element 28 and the illumination unit 29 is similar to the control in the frame period F13. In a case in which the light quantity is equal to or greater than a predetermined quantity in each frame period after the frame period F13, a state in which the LED 29a is turned off continues in a plurality of frame periods.

In a case in which the light quantity is less than the predetermined quantity, pixels 54 of two or more rows and less than V rows may constitute the light quantity detecting unit 28a.

Figure 11:
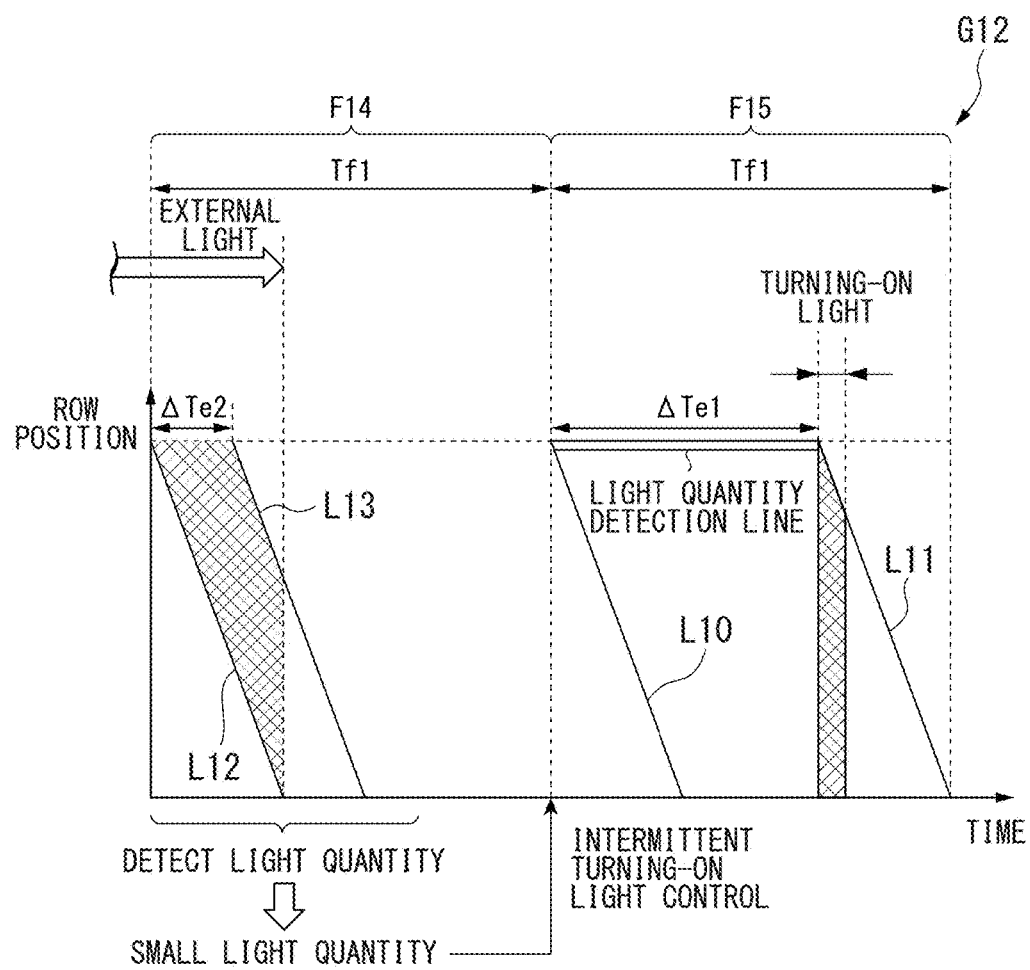
FIG. 11 is a timing chart showing the operation of the endoscope apparatus according to the first embodiment of the present invention.

FIG. 11 shows a third operation of the endoscope apparatus 1. In FIG. 11, a graph G12 shows a timing of the operation of each pixel 54 in an imaging area. In the graph G12, the horizontal direction represents the time, and the vertical direction represents the row position. The uppermost row is the first row, and the lowermost row is the V-th row. The length of the frame period, in other words, the display period of the monitor 4 is Tf1. A frame rate for displaying a live image is 1/Tf1.

The control of the imaging element 28 and the illumination unit 29 is executed for every frame period. In FIG. 11, operations in a frame period F14 and a frame period F15 among a plurality of continuous frame periods are shown. The control of the imaging element 28 and the illumination unit 29 in each frame period is based on a result of the detection of the light quantity in the previous frame period. When each frame period starts, the LED 29a is turned off.

In each frame period, the control unit 47 sets all of the pixels 54 disposed in the imaging area as the scanning area. In the pixels 54 of all of the rows disposed in the imaging area, resetting, transmission of electric charge, and signal reading are executed. By using block reading, signal reading may be executed only in the pixels 54 of a part of the columns disposed in the imaging area. In other words, resetting and transmission of electric charge are executed in the pixels 54 of all of the rows disposed in the imaging area, and signal reading may be executed in only pixels 54 of a part of the columns disposed in the imaging area.

The control of the imaging element 28 and the illumination unit 29 in the frame period F14 is similar to the control in the frame period F13. In a case in which the light quantity is equal to or greater than a predetermined quantity in the previous frame period of the frame period F14, in the frame period F14, the control unit 47 determines a light quantity on the basis of video signals generated from imaging signals output from all of the pixels 54 disposed in the imaging area. In other words, all of the pixels 54 disposed in the imaging area constitute the light quantity detecting unit 28a. On the basis of a result of the determination of the light quantity in the frame period F14, the operation executed in the frame period F15 is determined.

In a case in which the light quantity is less than a predetermined quantity in the frame period F14, in the frame period F15, the LED 29a is controlled to be intermittently turned on. The control of the imaging element 28 and the illumination unit 29 in the frame period F15 is similar to the control in the frame period F10. In a case in which the light quantity is less than a predetermined quantity in each frame period after the frame period F15, the operation in which LED 29a is intermittently turned on continues in a plurality of frame periods.

In a case in which the light quantity is less than the predetermined quantity, pixels 54 of two or more rows and less than V rows may constitute the light quantity detecting unit 28a.

Figure 12:
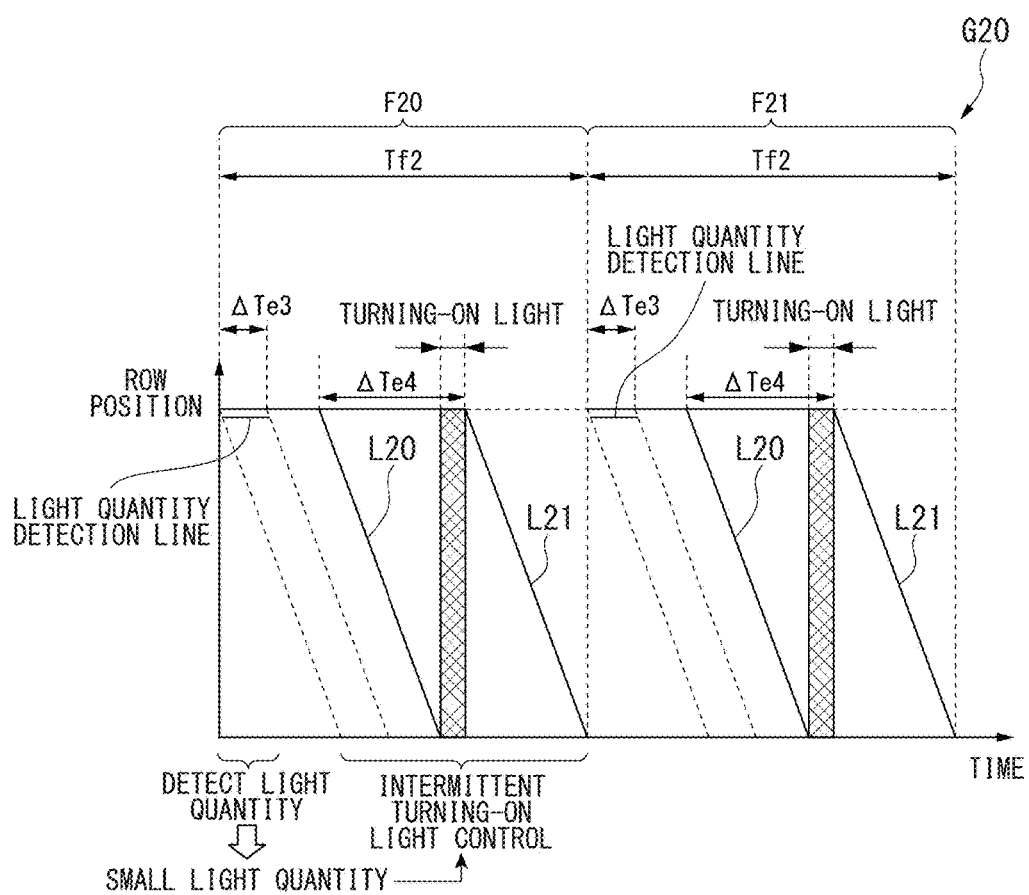
FIG. 12 is a timing chart showing the operation of the endoscope apparatus according to the first embodiment of the present invention.

FIG. 12 shows a fourth operation of the endoscope apparatus 1. In FIG. 12, a graph G20 shows a timing of the operation of each pixel 54 in an imaging area. In the graph G20, the horizontal direction represents the time, and the vertical direction represents the row position. The uppermost row is the first row, and the lowermost row is the V-th row. The length of the frame period, in other words, the display period of the monitor 4 is Tf2. A frame rate for displaying a live image is 1/Tf2.

The control of the imaging element 28 and the illumination unit 29 is executed for every frame period. In FIG. 12, operations in a frame period F20 and a frame period F21 among a plurality of continuous frame periods are shown. The control of the imaging element 28 and the illumination unit 29 in each frame period is based on a result of the detection of the light quantity in each frame period. When each frame period starts, the LED 29a is turned off.

In each frame period, the scanning of the pixels 54 is executed twice. In the scanning of the first time, the control unit 47 sets the pixels 54 of the first row disposed in the imaging area as the scanning area. In the pixels 54 of the first row disposed in the imaging area, resetting, transmission of electric charge, and signal reading are executed. By using block reading, signal reading may be executed only in the pixels 54 of a part of the columns in the first row. In other words, resetting and transmission of electric charge are executed in the pixels 54 of the first row disposed in the imaging area, and signal reading may be executed only in pixels 54 of a part of the columns in the first row disposed in the imaging area.

In the scanning of the first time, an exposure time is ΔTe3. The control unit 47 determines a light quantity on the basis of video signals generated from imaging signals output from the pixels 54 of the first row (light quantity detection line). In other words, the pixels 54 of the first row constitute the light quantity detecting unit 28a. On the basis of a result of the determination of the light quantity in the frame period F20, the operation executed in the frame period F20 is determined.

In a case in which the light quantity is less than a predetermined quantity in the frame period F20, in the frame period F20, the LED 29a is controlled to be intermittently turned on. In the frame period F20, in the scanning of the second time, the control unit 47 sets all of the pixels 54 disposed in the imaging area as the scanning area. In the pixels 54 of all of the rows disposed in the imaging area, resetting, transmission of electric charge, and signal reading are executed. By using block reading, signal reading may be executed only in the pixels 54 of a part of the columns disposed in the imaging area. In other words, resetting and transmission of electric charge may be executed in the pixels 54 of all of the rows disposed in the imaging area, and signal reading may be executed in only pixels 54 of a part of the columns disposed in the imaging area.

A straight line L20 represents an end timing of resetting in the pixels 54 of each row disposed in the imaging area, in other words, a start timing of exposure. A straight line L21 represents a start timing of transmission of electric charge in the pixels 54 of each row disposed in the imaging area, in other words, an end timing of exposure. The slope of the straight line L20 and the straight line L21 is based on the scanning rate. An exposure period is a period from a timing represented by the straight line L20 to a timing represented by the straight line L21. The length of the exposure period, in other words, the exposure time is ΔTe4. The exposure time ΔTe4 is longer than the exposure time ΔTe3.

The control of the imaging element 28 and the illumination unit 29 in the frame period F21 is similar to the control in the frame period F20. In a case in which a light quantity in each frame period is less than a predetermined quantity, the operation in which LED 29a is intermittently turned on continues in a plurality of frame periods.

Figure 13:
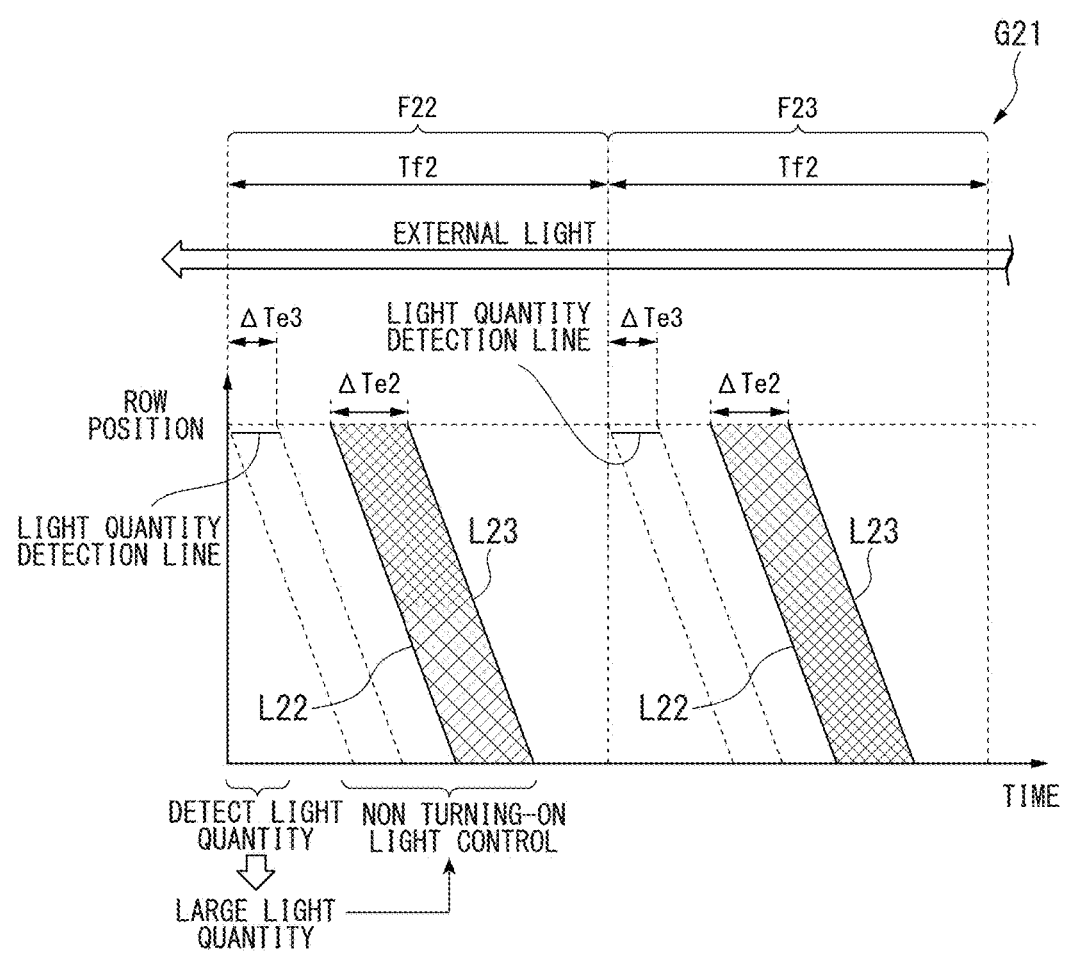
FIG. 13 is a timing chart showing the operation of the endoscope apparatus according to the first embodiment of the present invention.

FIG. 13 shows a fifth operation of the endoscope apparatus 1. In FIG. 13, a graph G21 shows a timing of the operation of each pixel 54 in an imaging area. In the graph G21, the horizontal direction represents the time, and the vertical direction represents the row position. The uppermost row is the first row, and the lowermost row is the V-th row. The length of the frame period, in other words, the display period of the monitor 4 is Tf2. A frame rate for displaying a live image is 1/Tf2.

The control of the imaging element 28 and the illumination unit 29 is executed for every frame period. In FIG. 13, operations in a frame period F22 and a frame period F23 among a plurality of continuous frame periods are shown. The control of the imaging element 28 and the illumination unit 29 in each frame period is based on a result of the detection of the light quantity in each frame period. When each frame period starts, the LED 29a is turned off.

In each frame period, the scanning of the pixels 54 is executed twice. In the scanning of the first time, the control unit 47 sets the pixels 54 of the first row disposed in the imaging area as the scanning area. In the pixels 54 of the first row disposed in the imaging area, resetting, transmission of electric charge, and signal reading are executed. By using block reading, signal reading may be executed only in the pixels 54 of a part of the columns in the first row. In other words, resetting and transmission of electric charge are executed in the pixels 54 of the first row disposed in the imaging area, and signal reading may be executed only in pixels 54 of a part of the columns in the first row disposed in the imaging area.

In the scanning of the first time, an exposure time is $\Delta Te3$. The control unit 47 determines a light quantity on the basis of video signals generated from imaging signals output from the pixels 54 of the first row (light quantity detection line). In other words, the pixels 54 of the first row constitute the light quantity detecting unit 28a. On the basis of a result of the determination of the light quantity in the frame period F22, the operation executed in the frame period F22 is determined.

In a case in which the light quantity is equal to or greater than a predetermined quantity in the frame period F22, in the frame period F22, the LED 29a is controlled to continue to be in a turned-off state. In the frame period F22, in the scanning of the second time, the control unit 47 sets all of the pixels 54 disposed in the imaging area as the scanning area. In the pixels 54 of all of the rows disposed in the imaging area, resetting, transmission of electric charge, and signal reading are executed. By using block reading, signal reading may be executed only in the pixels 54 of a part of the columns disposed in the imaging area. In other words, resetting and transmission of electric charge may be executed in the pixels 54 of all of the rows disposed in the imaging area, and signal reading may be executed in only pixels 54 of a part of the columns disposed in the imaging area.

A straight line L22 represents an end timing of resetting in the pixels 54 of each row disposed in the imaging area, in other words, a start timing of exposure. A straight line L23 represents a start timing of transmission of electric charge in the pixels 54 of each row disposed in the imaging area, in other words, an end timing of exposure. The slope of the straight line L22 and the straight line L23 is based on the scanning rate. The slope of the straight line L22 and the straight line L23 is the same as the slope of the straight line L20 and the straight line L21. An exposure period is a period from a timing represented by the straight line L22 to a timing represented by the straight line L23. The length of the exposure period, in other words, the exposure time is $\Delta Te2$. The exposure time $\Delta Te2$ is shorter than the exposure time $\Delta Te4$. The exposure time $\Delta Te2$ is longer than the exposure time $\Delta Te3$. The exposure time $\Delta Te2$ may be shorter than the exposure time $\Delta Te3$. The exposure time $\Delta Te2$ may be the same as the exposure time $\Delta Te3$.

The control of the imaging element 28 and the illumination unit 29 in the frame period F23 is similar to the control in the frame period F22. In a case in which a light quantity is equal to or greater than a predetermined quantity in each frame period, a state in which the LED 29a is turned off continues in a plurality of frame periods.

In the operations shown in the graph G20 and the graph G21, the endoscope apparatus 1 can execute determination of the light quantity and the control of the light source of the illumination unit 29 in one frame period by executing scanning twice in one frame period. For this reason, mismatch between the state of light in the surroundings of the imaging element 28 and the detail of control based on a result of the determination of the light quantity is reduced.

As described above, the control unit 47 may compare a sum of signal values of video signals corresponding to the imaging signals read from the pixels constituting the light quantity detecting unit 28a with a predetermined quantity.

In a case in which the light quantity detected by the light quantity detecting unit 28a is less than a predetermined quantity, the control unit 47 may set the exposure time of the pixels 54 to a first time ($\Delta Te1$). In a case in which the light quantity detected by the light quantity detecting unit 28a is equal to or greater than a predetermined quantity, the control unit 47 may set the exposure time of the pixels 54 to a second time ($\Delta Te2$) that is shorter than the first time (FIG. 10). After the exposure time of the pixels 54 is set to the second time, control unit 47, in a case in which the light quantity detected by the light quantity detecting unit 28a is less than the predetermined quantity, may set the exposure time of the pixels 54 to the first time (FIG. 11).

In a case in which the light quantity detected by the light quantity detecting unit 28a is equal to or greater than the predetermined quantity, the control unit 47 may set the exposure time of the pixels 54 to time corresponding to the light quantity (Step S120).

In a case in which the light quantity detected by the light quantity detecting unit 28a is less than the predetermined quantity in a first frame period, in a second frame period, the control unit 47 may control the imaging element 28 such that at least parts of the exposure periods of pixels 54 disposed in at least a part of the scanning area overlap each other (FIG. 11). The first frame period and the second frame period are continuous frame periods.

In a case in which the light quantity detected by the light quantity detecting unit 28a is equal to or greater than the predetermined quantity, the illumination control unit 46 may control the illumination unit 29 such that the light source is turned off.

In the frame period, first scanning (scanning of the first time) and second scanning (scanning of the second time) may be executed. The control unit 47 may set a scanning area for the first scanning and a scanning area for the second scanning in the imaging element 28. The light quantity detecting unit 28a may be pixels 54 disposed in at least one of a plurality of rows. The pixels 54 constituting the light quantity detecting unit 28a may constitute a scanning area for the first scanning In a case in which the light quantity detected by the light quantity detecting unit 28a is less than a predetermined quantity, the control unit 47 may control the imaging element 28 such that at least parts of exposure periods of pixels 54 disposed in at least a part of the scanning area for the second scanning overlap each other (FIG. 12).

All of the pixels 54 disposed in the imaging area may constitute the scanning area for the second scanning The control unit 47 may set the exposure time of the pixels 54 of the scanning area in the first scanning to a third time (ΔTe3). In a case in which the light quantity detected by the light quantity detecting unit 28a is less than a predetermined quantity, the control unit 47 may set the exposure time of the pixels 54 of the scanning area in the second scanning to a first time (ΔTe4) that is longer than the third time (FIG. 12).

In a case in which the light quantity detected by the light quantity detecting unit 28a is equal to or greater than a predetermined quantity, the illumination control unit 46 may control the illumination unit 29 such that the light source is turned off in the second scanning The control unit 47 may control the imaging element 28 such that imaging signals are read only from pixels 54 of a part of the columns disposed in the imaging area in the second scanning In a case in which the light quantity detected by the light quantity detecting unit 28a is less than a predetermined quantity, the control unit 47 may set the exposure time of the pixels 54 of the scanning area in the second scanning to a first time (ΔTe4). In a case in which the light quantity detected by the light quantity detecting unit 28a is equal to or greater than a predetermined quantity, the control unit 47 may set the exposure time of the pixels 54 of the scanning area in the second scanning to a second time (ΔTe2) that is shorter than the first time. In a case in which the light quantity detected by the light quantity detecting unit 28a is equal to or greater than a predetermined quantity, the illumination control unit 46 may control the illumination unit 29 such that the light source is turned off in the second scanning (FIGS. 12 and 13).

In the first embodiment, in a case in which the light quantity detected by the light quantity detecting unit 28a is equal to or less than a predetermined quantity, the control unit 47 controls the imaging element 28 such that at least parts of exposure periods of pixels 54 disposed in at least a part of the scanning area overlap each other. In a case in which the light quantity detected by the light quantity detecting unit 28a is equal to or less than a predetermined quantity, the illumination control unit 46 controls the illumination unit 29 such that the light source is turned on in a period in which at least parts of exposure periods of pixels 54 disposed in at least a part of the scanning area overlap each other. For this reason, the endoscope apparatus 1 can acquire an image in which the distortion of the subject is reduced.

In a case in which the light quantity detected by the light quantity detecting unit 28a is less than a predetermined quantity, by turning off the illumination unit 29, the endoscope apparatus 1 can reduce the generation of blown-out-highlights in an image. In addition, the endoscope apparatus 1 can reduce the power consumption.

The control unit 47 may set the scanning area only in a part of the imaging area. In such a case, the processing load of the CPU 18 required for reading imaging signals is reduced.

(Second Embodiment)

Figure 14:
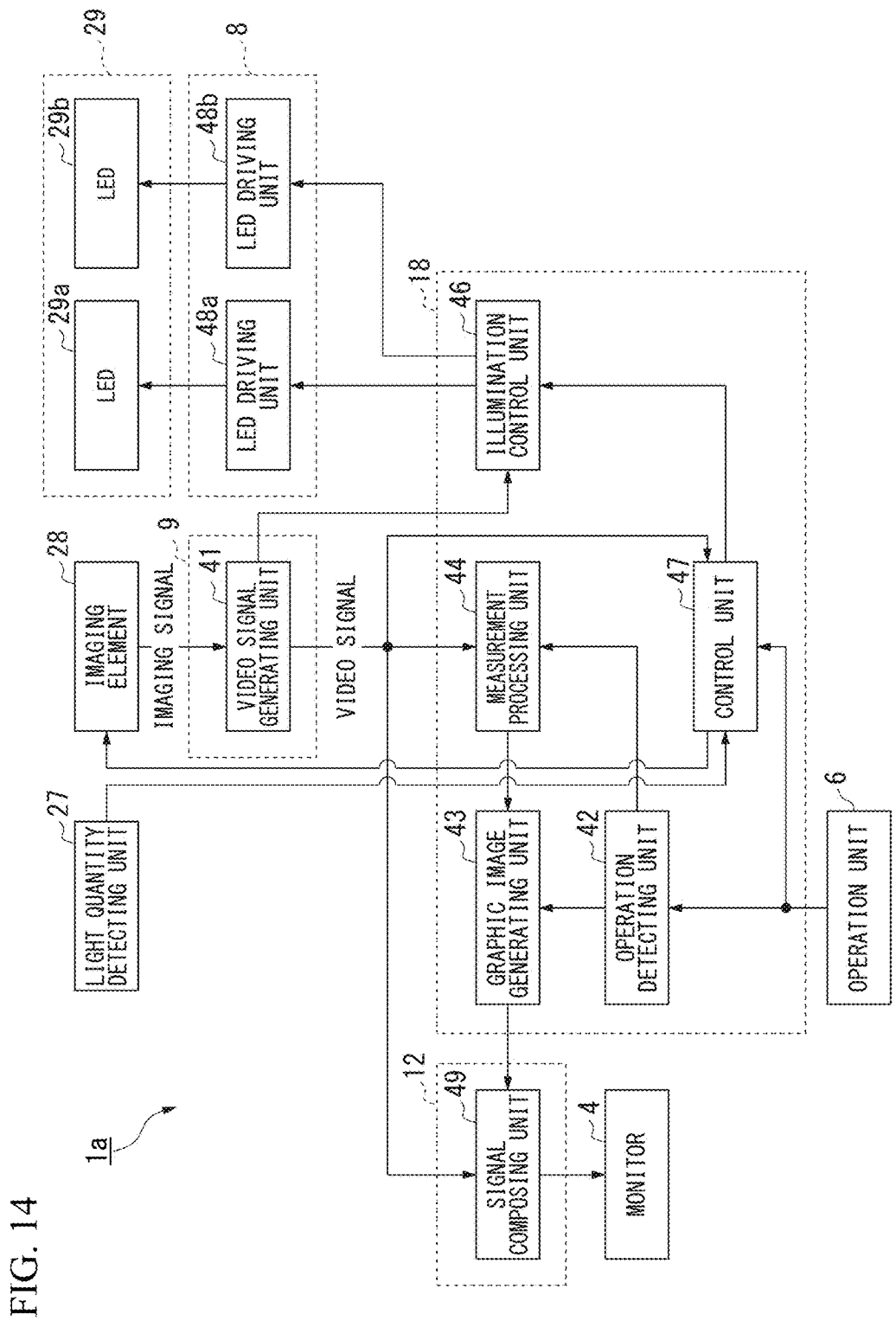
FIG. 14 is a block diagram showing a configuration regarding major functions of an endoscope apparatus according to a second embodiment of the present invention.

In a second embodiment of the present invention, the configuration of the endoscope apparatus 1 shown in FIG. 3 is changed to an endoscope apparatus 1a shown in FIG. 14.

FIG. 14 shows a configuration regarding major functions of the endoscope apparatus 1a. As shown in FIG. 14, the endoscope apparatus 1a includes a monitor 4 (display unit), an operation unit 6, a light quantity detecting unit 27, an imaging element 28 (imaging unit), an LED 29a, an LED 29b, a video signal generating unit 41, an operation detecting unit 42, a graphic image generating unit 43, a measurement processing unit 44, an illumination control unit 46, a control unit 47 (imaging control unit), an LED driving unit 48a, an LED driving unit 48b, and a signal composing unit 49.

In the configuration shown in FIG. 14, differences from the configuration shown in FIG. 3 will be described. In the endoscope apparatus 1a, the light quantity detecting unit 27 is a device that is independently arranged from the imaging element 28. For example, the light quantity detecting unit 27 is a photo detector. The light quantity detecting unit 27 is disposed in a tip end part 21. The light quantity detecting unit 27 is disposed near the imaging element 28. The light quantity detecting unit 27 may be in contact with the imaging element 28. The light quantity detecting unit 27 may be disposed on the surface of the imaging element 28. The light quantity detecting unit 27 detects a light quantity at a place in which the imaging element 28 is disposed. In the configuration shown in FIG. 14, the other points are similar to those of the configuration shown in FIG. 3.

The operation of the endoscope apparatus 1a according to the second embodiment is similar to that of the endoscope apparatus 1 according to the first embodiment. For this reason, the operation of the endoscope apparatus 1a will not be described here.

In the second embodiment, similar to the first embodiment, the endoscope apparatus 1a can acquire an image in which the distortion of a subject is reduced.

While preferred embodiments of the invention have been described and shown above, it should be understood that these are exemplars of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope apparatus comprising:
   an imaging element configured to generate imaging signals by imaging a subject and include a plurality of pixels disposed in a matrix pattern, an imaging area in which the plurality of pixels are disposed including a scanning area, the imaging signals being read from at least a part of the pixels in each row in the scanning area;
   a video signal generating circuit configured to generate video signals from the imaging signals;
   an illuminator comprising a light source configured to generate illumination light emitted to the subject;
   a light quantity detector configured to detect a light quantity at a place in which the imaging element is disposed; and
   one or more processors comprising hardware, wherein the processor is configured to:
      control the imaging element such that at least parts of exposure periods of the pixels disposed in at least a part of the scanning area overlap each other, in a case in which the light quantity detected by the light quantity detector is less than a predetermined quantity;

control the illuminator such that the light source is turned on in a period in which at least parts of the exposure periods of the pixels disposed in at least a part of the scanning area overlap each other, in a case in which the light quantity detected by the light quantity detector is less than the predetermined quantity;

set an exposure time that is a length of the exposure period of the pixels to a second time that is shorter than a first time, in a case in which the light quantity detected by the light quantity detector is equal to or greater than the predetermined quantity; and set the exposure time of the pixels to the first time, in a case in which the light quantity detected by the light quantity detector is less than the predetermined quantity, after the exposure time of the pixels is set to the second time.

2. The endoscope apparatus according to claim 1, wherein the light quantity detector is at least a part of the plurality of the pixels.

3. The endoscope apparatus according to claim 1, wherein the light quantity detector is a device disposed independently from the imaging element.

4. The endoscope apparatus according to claim 2, wherein the one or more processors are configured to compare a sum of signal values of the video signals corresponding to the imaging signals read from the pixels constituting the light quantity detector with the predetermined quantity.

5. The endoscope apparatus according to claim 1, wherein the one or more processors are configured to set the exposure time of the pixels to the second time corresponding to the light quantity detected by the light quantity detector, in a case in which the light quantity is equal to or greater than the predetermined quantity.

6. The endoscope apparatus according to claim 1, wherein the one or more processors are configured to control the imaging element such that at least parts of the exposure periods of the pixels disposed in at least a part of the scanning area overlap each other in a second frame period, in a case in which the light quantity detected by the light quantity detector in a first frame period is less than the predetermined quantity, the first frame period and the second frame period being continuous frame periods.

7. The endoscope apparatus according to claim 1, wherein the one or more processors are configured to control the illuminator such that the light source is turned off, in a case in which the light quantity detected by the light quantity detector is equal to or greater than the predetermined quantity.

8. The endoscope apparatus according to claim 1, wherein first scanning and second scanning are executed in a frame period,
wherein the one or more processors are configured to set the scanning area of the first scanning and the scanning area of the second scanning in the imaging element,
wherein the light quantity detector is the pixels disposed in at least one of a plurality of rows,
wherein the pixels constituting the light quantity detector constitute the scanning area of the first scanning, and
wherein the one or more processors are configured to control the imaging element such that at least parts of the exposure periods of the pixels disposed in at least a part of the scanning area of the second scanning overlap each other, in a case in which the light quantity detected by the light quantity detector is less than the predetermined quantity.

9. The endoscope apparatus according to claim 8, wherein all of the pixels disposed in the imaging area constitute the scanning area of the second scanning.

10. The endoscope apparatus according to claim 8, wherein the one or more processors are configured to set the exposure time of the pixels of the scanning area of the first scanning to a third time, and
wherein the one or more processors are configured to set the exposure time of the pixels of the scanning area of the second scanning to the first time that is longer than the third time, in a case in which the light quantity detected by the light quantity detector is less than the predetermined quantity.

11. The endoscope apparatus according to claim 9, wherein the one or more processors are configured to control the illuminator such that the light source is turned off in the second scanning, in a case in which the light quantity detected by the light quantity detector is equal to or greater than the predetermined quantity, and
wherein the one or more processors are configured to control the imaging element such that the imaging signals are read only from the pixels of a part of columns disposed in the imaging area in the second scanning.

12. The endoscope apparatus according to claim 8, wherein the one or more processors are configured to set the exposure time of the pixels of the scanning area of the second scanning to the first time, in a case in which the light quantity detected by the light quantity detector is less than the predetermined quantity,
wherein the one or more processors are configured to set the exposure time of the pixels of the scanning area of the second scanning to the second time, in a case in which the light quantity detected by the light quantity detector is equal to or greater than the predetermined quantity, and
wherein the one or more processors are configured to control the illuminator such that the light source is turned off in the second scanning, in a case in which the light quantity detected by the light quantity detector is equal to or greater than the predetermined quantity.

13. A method of operating an endoscope apparatus, the method comprising:
a first step;
a second step;
a third step; and
a fourth step,
wherein the endoscope apparatus comprises:
an imaging element configured to generate imaging signals by imaging a subject and include a plurality of pixels disposed in a matrix pattern, an imaging area in which the plurality of pixels are disposed including a scanning area, the imaging signals being read from at least a part of the pixels in each row in the scanning area;
a video signal generating circuit configured to generate video signals from the imaging signals;
an illuminator comprising a light source configured to generate illumination light emitted to the subject;
a light quantity detector configured to detect a light quantity at a place in which the imaging element is disposed; and
one or more processors comprising hardware, and wherein the method comprises:
controlling, by the one or more processors, the imaging element such that at least parts of exposure periods of the pixels disposed in at least a part of the scanning area overlap each other in the first step, in a case in which the light quantity detected by the light quantity detector is less than a predetermined quantity;
controlling, by the one or more processors, the illuminator such that the light source is turned on in a period in which at least parts of the exposure periods of the pixels disposed in at least a part of the scanning area overlap each other in the second step, in a case in which the light quantity detected by the light quantity detector is less than the predetermined quantity;
setting, by the one or more processors, an exposure time that is a length of the exposure period of the pixels to a second time that is shorter than a first time in the third step, in a case in which the light quantity detected by the light quantity detector is equal to or greater than the predetermined quantity; and
setting, by the one or more processors, the exposure time of the pixels to the first time in the fourth step, in a case in which the light quantity detected by the light quantity detector is less than the predetermined quantity, after the exposure time of the pixels is set to the second time.

14. A non-transitory computer-readable recording medium having a program for operating an endoscope apparatus to execute a first step, a second step, a third step, and a fourth step recorded thereon,
wherein the endoscope apparatus comprises:
an imaging element configured to generate imaging signals by imaging a subject and include a plurality of pixels disposed in a matrix pattern, an imaging area in which the plurality of pixels are disposed including a scanning area, the imaging signals being read from at least a part of the pixels in each row in the scanning area;
a video signal configured to generate circuit generating video signals from the imaging signals;
an illuminator comprising a light source configured to generate illumination light emitted to the subject;
a light quantity detector configured to detect a light quantity at a place in which the imaging element is disposed; and
one or more processors comprising hardware,
wherein the program causes one or more processors to:
control the imaging element such that at least parts of exposure periods of the pixels disposed in at least a part of the scanning area overlap each other in the first step, in a case in which the light quantity detected by the light quantity detector is less than a predetermined quantity;
control the illuminator such that the light source is turned on in a period in which at least parts of the exposure periods of the pixels disposed in at least a part of the scanning area overlap each other in the second step, in a case in which the light quantity detected by the light quantity detector is equal to or greater than the predetermined quantity;
set an exposure time that is a length of the exposure period of the pixels to a second time that is shorter than a first time in the third step, in a case in which the light quantity detected by the light quantity detector is less than the predetermined quantity; and
set the exposure time of the pixels to the first time in the fourth step, in a case in which the light quantity detected by the light quantity detector is less than the predetermined quantity, after the exposure time of the pixels is set to the second time.

* * * * *